(12) United States Patent
Pfau et al.

(10) Patent No.: US 8,598,190 B2
(45) Date of Patent: Dec. 3, 2013

(54) 3H-IMIDAZO [4, 5-C] PYRIDINE-6-CARBOXAMIDES AS ANTI-INFLAMMATORY AGENTS

(75) Inventors: Roland Pfau, Biberach (DE); Kirsten Arndt, Ravensburg (DE); Henri Doods, Warthausen (DE); Norbert Hauel, Schemmerhofen (DE); Klaus Klinder, Oggelshausen (DE); Raimund Kuelzer, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 269 days.

(21) Appl. No.: 13/119,832

(22) PCT Filed: Sep. 25, 2009

(86) PCT No.: PCT/EP2009/062424
§ 371 (c)(1),
(2), (4) Date: Jun. 7, 2011

(87) PCT Pub. No.: WO2010/034798
PCT Pub. Date: Apr. 1, 2010

(65) Prior Publication Data
US 2011/0275656 A1 Nov. 10, 2011

(30) Foreign Application Priority Data
Sep. 25, 2008 (EP) .................... 08165120

(51) Int. Cl.
| | | |
|---|---|---|
| A61K 31/437 | (2006.01) | |
| A61K 31/444 | (2006.01) | |
| A61P 11/06 | (2006.01) | |
| A61P 11/00 | (2006.01) | |
| A61P 1/00 | (2006.01) | |
| A61P 35/00 | (2006.01) | |
| C07D 471/04 | (2006.01) | |

(52) U.S. Cl.
USPC .............. 514/278; 514/303; 546/15; 546/118

(58) Field of Classification Search
USPC .............................. 514/278, 303; 546/118, 15
See application file for complete search history.

(56) References Cited

U.S. PATENT DOCUMENTS

| | | | |
|---|---|---|---|
| 4,929,623 A | 5/1990 | Abe et al. | |
| 6,608,084 B1 | 8/2003 | Bourzat et al. | |
| 2004/0198768 A1 | 10/2004 | Choo et al. | |
| 2005/0267147 A1 | 12/2005 | Poitout et al. | |
| 2006/0173036 A1 | 8/2006 | Poitout et al. | |
| 2006/0287344 A1 | 12/2006 | Albers et al. | |
| 2007/0060598 A1 | 3/2007 | Albers et al. | |
| 2010/0004301 A1 | 1/2010 | Pelcman et al. | |
| 2010/0256188 A1 | 10/2010 | Pfau et al. | |
| 2011/0275656 A1 | 11/2011 | Pfau et al. | |
| 2011/0312935 A1 | 12/2011 | Pfau et al. | |
| 2012/0115902 A1 | 5/2012 | Pfau et al. | |
| 2012/0122930 A1 | 5/2012 | Pfau et al. | |
| 2012/0149676 A1 | 6/2012 | Priepke et al. | |
| 2012/0196897 A1 | 8/2012 | Pfau et al. | |
| 2012/0208839 A1 | 8/2012 | Priepke et al. | |
| 2012/0214786 A1 | 8/2012 | Priepke et al. | |
| 2012/0309738 A1 | 12/2012 | Priepke et al. | |
| 2012/0309755 A1 | 12/2012 | Priepke et al. | |

FOREIGN PATENT DOCUMENTS

| | | |
|---|---|---|
| EP | 0034743 A1 | 9/1981 |
| EP | 0295656 A1 | 12/1988 |
| EP | 0419210 A1 | 3/1991 |
| EP | 1069124 A1 | 1/2001 |
| FR | 2851563 A1 | 8/2004 |
| FR | 2852957 A1 | 10/2004 |
| WO | 00/15612 A1 | 3/2000 |
| WO | 00/49005 A1 | 8/2000 |
| WO | 00/61580 A1 | 10/2000 |
| WO | 00/68213 A1 | 11/2000 |
| WO | 01/25238 A1 | 4/2001 |
| WO | 03/053939 A1 | 7/2003 |
| WO | 03/074515 A1 | 9/2003 |
| WO | 3/082272 A1 | 10/2003 |
| WO | 2004/005323 A1 | 1/2004 |
| WO | 2004/035740 A1 | 4/2004 |
| WO | 2004/072068 A1 | 8/2004 |

(Continued)

OTHER PUBLICATIONS

D.J. Gale et al., The Amidomethylation of Some N,N-Dialkylanilines; Aust.J. Chem.; pp. 2447-2458; vol. 28; 1975.
International Search Report Form PCT/ISA/210 and Written Opinion Form PCT/ISA/237 for corresponding PCT/EP2009/062424; date of mailing: Dec. 10, 2009.
European Search Report, for corresponding application No. EP 08 16 5120; date of mailing: May 6, 2009.
R.D. Carpenter et al., Carbodiimide-based benzinidazole library method, Journal of Combinatorial Chemistry, Oct. 27, 2006, pp. 907-914, vol. 8, No. 6.

(Continued)

*Primary Examiner* — Niloofar Rahmani
(74) *Attorney, Agent, or Firm* — Michael P. Morris; Philip I. Datlow

(57) ABSTRACT

There are provided compounds of formula (I), wherein $R^1$, $R^6$, $R^8$, $Q^2$, $Q^3$, $Q^{3a}$, $Q^4$, L and A have meanings given in the description, and pharmaceutically-acceptable salts thereof, which compounds are useful in the treatment of diseases in which inhibition of the activity of a member of the MAPEG family is desired and/or required, and particularly in the treatment of inflammation and/or cancer.

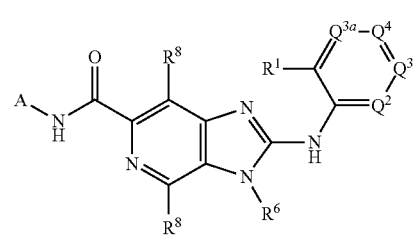

18 Claims, No Drawings

(56) References Cited

FOREIGN PATENT DOCUMENTS

| | | |
|---|---|---|
| WO | 2004/085425 A1 | 10/2004 |
| WO | 2004/089951 A1 | 10/2004 |
| WO | 2005/044793 A1 | 5/2005 |
| WO | 2005070906 A1 | 8/2005 |
| WO | 2005070920 A1 | 8/2005 |
| WO | 2005/123674 A1 | 12/2005 |
| WO | 2006/077366 A1 | 7/2006 |
| WO | 2006/090167 A1 | 8/2006 |
| WO | 2007/095124 A1 | 8/2007 |
| WO | 2007/127382 A1 | 11/2007 |
| WO | 2008/009924 A1 | 1/2008 |
| WO | 2008/035956 A1 | 3/2008 |
| WO | 2008/071944 A1 | 6/2008 |
| WO | 2008/129276 A | 10/2008 |
| WO | 2010034796 A1 | 4/2010 |
| WO | 2010034797 A1 | 4/2010 |
| WO | 2010034798 A1 | 4/2010 |
| WO | 2010034799 A1 | 4/2010 |
| WO | 2010100249 A1 | 9/2010 |

OTHER PUBLICATIONS

Lala et al., Cancer and Metastasis reviews (1998), 17 (1), 91-106.
Golub et al., Science (1999), vol. 286, 531-537.
Cancer [online], [retrieved on Jul. 6, 2007]. Retrieved from the Internet, URL http://www.nlm.nih.gov/medlineplus/cancer.html>.
Cancer [online], [retrieved on Jul. 6, 2007]. Retrieved from the Internet, URL http://en.wikipedia.org/wikilCancer.
Silverman et al., the Organic Chemistry of Drug Design and Drug Action, Chapter 2: Drug Discovery, Design, and Development, Academic Press, p. 5-51, 1992.
Samuelsson et al., Pharmacology Review, vol. 59, No. 3, pp. 207-224, 2007.

3H-IMIDAZO [4, 5-C] PYRIDINE-6-CARBOXAMIDES AS ANTI-INFLAMMATORY AGENTS

FIELD OF THE INVENTION

This invention relates to novel pharmaceutically-useful compounds, which compounds are useful as inhibitors of enzymes belonging to the membrane-associated proteins in the eicosanoid and glutathione metabolism (MAPEG) family. Members of the MAPEG family include the microsomal prostaglandin E synthase-1 (mPGES-1), 5-lipoxygenase-activating protein (FLAP), leukotriene $C_4$ synthase and microsomal glutathione S-transferases (MGST1, MGST2 and MGST3). The compounds are of potential utility in the treatment of inflammatory diseases including respiratory diseases. The invention also relates to the use of such compounds as medicaments, to pharmaceutical compositions containing them, and to synthetic routes for their production.

BACKGROUND OF THE INVENTION

There are many diseases/disorders that are inflammatory in their nature. One of the major problems associated with existing treatments of inflammatory conditions is a lack of efficacy and/or the prevalence of side effects (real or perceived).

Inflammatory diseases that affect the population include asthma, inflammatory bowel disease, rheumatoid arthritis, osteoarthritis, rhinitis, conjunctivitis and dermatitis. Inflammation is also a common cause of pain. Inflammatory pain may arise for numerous reasons, such as infection, surgery or other trauma. Moreover, several diseases including malignancies and cardiovascular diseases are known to have inflammatory components adding to the symptomotology of the patients.

Asthma is a disease of the airways that contains elements of both inflammation and bronchoconstriction. Treatment regimens for asthma are based on the severity of the condition. Mild cases are either untreated or are only treated with inhaled R-agonists which affect the bronchoconstriction element, whereas patients with more severe asthma typically are treated regularly with inhaled corticosteroids which to a large extent are anti-inflammatory in their nature.

Another common disease of the airways with inflammatory and bronchoconstrictive components is chronic obstructive pulmonary disease (COPD). The disease is potentially lethal, and the morbidity and mortality from the condition is considerable. At present, there is no known pharmacological treatment capable of changing the course of the disease.

The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever and pain. Consequently, numerous drugs have been developed with a view to inhibiting the formation of $PGE_2$, including "NSAIDs" (non-steroidal anti-inflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects. For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that inhibits (preferably selectively) the transformation of $PGH_2$ to the pro-inflammatory mediator $PGE_2$ might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described.

The leukotrienes (LTs) are formed from arachidonic acid by a set of enzymes distinct from those in the COX/PGES pathway. Leukotriene $B_4$ is known to be a strong proinflammatory mediator, while the cysteinyl-containing leukotrienes $C_4$, $D_4$ and $E_4$ (CysLTs) are mainly very potent bronchoconstrictors and have thus been implicated in the pathobiology of asthma. The biological activities of the CysLTs are mediated through two receptors designated $CysLT_1$ and $CysLT_2$. As an alternative to steroids, leukotriene receptor antagonists (LTRas) have been developed in the treatment of asthma. These drugs may be given orally, but do not control inflammation satisfactorily. The presently used LTRas are highly selective for $CysLT_1$. It may be hypothesised that better control of asthma, and possibly also COPD, may be attained if the activity of both of the CysLT receptors could be reduced. This may be achieved by developing unselective LTRas, but also by inhibiting the activity of proteins, e.g. enzymes, involved in the synthesis of the CysLTs. Among these proteins, 5-lipoxygenase, 5-lipoxygenase-activating protein (FLAP), and leukotriene $C_4$ synthase may be mentioned. A FLAP inhibitor would also decrease the formation of the proinflammatory $LTB_4$.

mPGES-1, FLAP and leukotriene $C_4$ synthase belong to the membrane-associated proteins in the eicosanoid and glutathione metabolism (MAPEG) family. Other members of this family include the microsomal glutathione S-transferases (MGST1, MGST2 and MGST3). For a review, c.f. P.-J. Jacobsson et al in *Am. J. Respir. Crit. Care Med.* 161, S20 (2000). It is well known that compounds prepared as antagonists to one of the MAPEGs may also exhibit inhibitory activity towards other family members, c.f. J. H Hutchinson et al in *J. Med. Chem.* 38, 4538 (1995) and D. Claveau et al in *J. Immunol.* 170, 4738 (2003). The former paper also describes that such compounds may also display notable cross-reactivity with proteins in the arachidonic acid cascade that do not belong to the MAPEG family, e.g. 5-lipoxygenase.

Thus, agents that are capable of inhibiting the action of mPGES-1, and thus reducing the formation of the specific arachidonic acid metabolite $PGE_2$, are likely to be of benefit in the treatment of inflammation. Further, agents that are capable of inhibiting the action of the proteins involved in the synthesis of the leukotrienes are also likely to be of benefit in the treatment of asthma and COPD.

In addition to their anti-inflammatory effect, mPGES-1 inhibitors are also known to be of potential use in treating or preventing a neoplasia, for example as described in international patent application WO 2007/124589. The rationale behind this may stem from the fact that the production of PGE2 is believed to promote the formation, growth and/or metastasis of neoplasias. As mPGES-1 is often expressed with COX-2 in benign and cancerous neoplasias, the inhibition of mPGES-1 (rather than COX-2) may cause the reduction of PGE2 and therefore mPGES-1 inhibitors may be useful the treatment of benign or malignant neoplasias.

The listing or discussion of an apparently prior-published document in this specification should not necessarily be taken as an acknowledgement that the document is part of the state of the art or is common general knowledge.

The synthesis of various benzimidazoles has been disclosed by Carpenter et al in the *Journal of Combinatorial Chemistry* (2006), 8(6), 907-914. However, no apparent medical use has been ascribed to such compounds.

DISCLOSURE OF THE INVENTION

There is provided a compound of formula I,

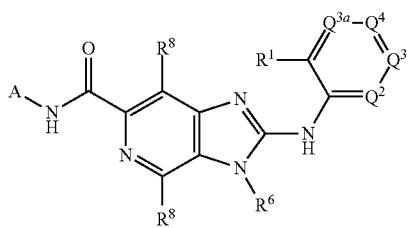

I in which
Q$^2$, Q$^3$, Q$^{3a}$ and Q$^4$ respectively represent —C(R$^2$)=, —C(R$^3$)=, —C(R$^{3a}$)= and —C(R$^4$)=; or
any one or two of Q$^2$, Q$^3$, Q$^{3a}$ and Q$^4$ may alternatively and independently represent —N=;
R$^1$ represents halo, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$, —C(O)R$^{y15}$;
C$_{1-7}$ alkyl, C$_{2-7}$ alkenyl, C$_{2-7}$ alkynyl, cycloalkyl [which latter four groups are optionally substituted by one or more substituents selected from fluoro, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and —C(O)R$^{y15}$]; or heterocycloalkyl or heteroaryl (which latter two groups are optionally substituted by one or more substituents selected from R$^9$);
R$^2$, R$^3$, R$^{3a}$ and R$^4$
independently represent hydrogen, halo, —CN, —N(R$^{y1}$)R$^{y2}$, —N(R$^{y3}$)—O(O)—R$^{y4}$, —N(R$^{y6}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$—R$^{y12}$, —S(O)$_2$N(R$^{y13}$)R$^{y14}$, —C(O)R$^{y15}$;
C$_{1-7}$ alkyl, C$_{2-7}$ alkenyl, C$_{2-7}$ alkynyl, cycloalkyl [which latter four groups are optionally substituted by one or more substituents selected from fluoro, —CN, —N(R$^{y1}$)R$^{y2}$, —N(R$^{y6}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and —C(O)R$^{y16}$] provided that if R$^3$ or R$^{3a}$ is a substituted C$_1$ alkyl group, then the substituent cannot be —N(R$^{y6}$)—S(O)$_2$—R$^{y6}$;
or any adjacent pair of R$^1$, R$^2$, R$^3$, R$^{3a}$ and R$^4$ (i.e. R$^1$ and R$^{3a}$, R$^2$ and R$^3$, R$^3$ and R$^4$ and R$^4$ and R$^{3a}$) may be linked together to form, along with the essential carbon atoms of the Q$^2$ to Q$^4$-containing ring to which they are necessarily attached, a further 5- to 7-membered ring, optionally containing one to three heteroatoms, which ring may contain one or two further unsaturations and which is optionally substituted by one or more C$_{1-3}$ alkyl and/or =O substituents;
R$^6$ represents hydrogen;
heterocycloalkyl, aryl, heteroaryl (which latter three groups are optionally substituted by one or more substituents selected from R$^9$); or
C$_{1-6}$ alkyl, C$_{2-6}$ alkenyl, C$_{2-6}$ alkynyl, cycloalkyl, which latter four groups are optionally substituted by one or more substituents selected from fluoro, —N(R$^{y1}$)R$^{y2}$, —N(R$^{y3}$)—O(O)—R$^{y4}$, —N(R$^{y6}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$N(R$^{y13}$)R$^{y14}$, —C(O)R$^{y15}$, heterocycloalkyl, cycloalkyl, aryl and heteroaryl (which latter four groups are optionally substituted by one or more substituents selected from R$^9$);
each R$^8$ independently represents hydrogen, halo, —N(R$^{y1}$)R$^{y2}$, —OR$^{y10}$, —S(O)$_2$—R$^{y11}$;
C$_{1-6}$ alkyl, C$_{2-6}$ alkenyl, C$_{2-6}$ alkynyl, cycloalkyl, —O—C$_{1-6}$ alkyl, —O—C$_{2-6}$ alkenyl, —O—C$_{2-6}$ alkynyl, —O-cycloalkyl, —O-heterocycloalkyl [which latter nine groups are optionally substituted by one or more substituents selected from fluoro, —CN, —N(R$^{y1}$)R$^{y2}$, —N(R$^{y3}$)—C(O)—R$^{y4}$, —N(R$^{y6}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$, —C(O)R$^{y16}$, cycloalkyl, heterocycloalkyl, aryl and heteroaryl (which latter four groups are optionally substituted by one or more substituents selected from R$^9$)];
heterocycloalkyl or heteroaryl (which latter two groups are optionally substituted by one or more substituents selected from R$^9$);
A represents aryl, heteroaryl, heterocycloalkyl, cycloalkyl, C$_{1-12}$ alkyl, C$_{2-12}$ alkenyl or C$_{2-12}$ alkynyl, all of which are optionally substituted by one or more substituents selected from R$^9$;
R$^9$ represents, on each occasion when used herein:
halo, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and —C(O)R$^{y15}$;
C$_{1-7}$ alkyl, C$_{2-7}$ alkenyl, C$_{2-7}$ alkynyl, cycloalkyl, heterocycloalkyl [which latter five groups are optionally substituted by one or more substituents selected from fluoro, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{11}$, —S(O)$_2$O—R$^{y12}$, —S(O)$_2$N(R$^{y13}$)R$^{y14}$ and —C(O)R$^{y15}$]; or
aryl or heteroaryl [which latter two groups are optionally substituted by one or more substituents selected from halo, —CN, C$_{1-7}$ alkyl, C$_{2-7}$ alkenyl, C$_{2-7}$ alkynyl, cycloalkyl (which latter four groups are optionally substituted by one or more substituents selected from fluoro and —OR$^{x2}$), —O—C$_{1-7}$ alkyl, —O—C$_{2-7}$ alkenyl, —O—C$_{2-7}$ alkynyl and —O-cycloalkyl (which latter four groups are optionally substituted by one or more fluoro atoms)]; or
any two R$^9$ substituents:
when attached to the adjacent atoms of the A group; and, in the case where the R$^9$ substituents are attached to a non-aromatic A group, when attached to the same atoms, may be linked together to form, together with the essential atoms of the A group to which the relevant $R^9$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or =O substituents;

m represents 0, 1 or 2;

each $R^{y4}$, $R^{y6}$, $R^{y11}$ and $R^{y15}$:

independently represent $C_{1-7}$ alkyl, $C_{2-7}$ alkenyl, $C_{2-7}$ alkynyl, cycloalkyl, which latter four groups are optionally substituted by one or more fluoro atoms;

each $R^{x2}$, $R^{y1}$, $R^{y2}$, $R^{y3}$, $R^{y5}$, $R^{y7}$, $R^{y8}$, $R^{y9}$, $R^{y10}$, $R^{y12}$, $R^{y13}$, and $R^{y14}$:

independently represent hydrogen or $C_{1-7}$ alkyl, $C_{2-7}$ alkenyl, $C_{2-7}$ alkynyl, cycloalkyl, heterocycloalkyl, which latter five groups are optionally substituted one or more substituents selected from fluoro and —$OC_{1-3}$ alkyl; or any two groups, when attached to the same nitrogen atom (i.e. $R^{y1}$ and $R^{y2}$, $R^{y8}$ and $R^{y9}$, and $R^{y13}$ and $R^{y14}$), may, together with that nitrogen atom to which they are necessarily attached, be linked together to form a 3- to 8-membered ring, optionally containing one or two further heteroatoms and which ring optionally contains one or two unsaturations and is optionally substituted by one or more $C_{1-3}$ alkyl and/or =O substituents, or a pharmaceutically acceptable salt thereof, which compounds are hereinafter referred to as 'the compounds of the invention'.

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention. For instance, a compound containing the moiety "1H-benzimidazole" may be considered to be identical to a corresponding compound containing a "3H-benzimidazole" moiety.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise specified, $C_{1-q}$ alkyl, and $C_{1-q}$ alkylene, groups (where q is the upper limit of the range), defined herein may be straight-chain or, when there is a sufficient number (i.e. a minimum of two or three, as appropriate) of carbon atoms, be branched-chain. For the avoidance of doubt, such groups are fully saturated.

Unless otherwise specified, $C_{2-q}$ alkenyl, and $C_{2-q}$ alkenylene, groups (where q is the upper limit of the range) refer to a hydrocarbon chain (in the case of alkenylene, the chain links two moieties) containing one or more double bond. Such groups as defined herein may be straight-chain or, when there is a sufficient number (i.e. a minimum of two or three, as appropriate) of carbon atoms, be branched-chain.

Unless otherwise specified, $C_{2-q}$ alkynyl, and $C_{2-q}$ alkynylene, groups (where q is the upper limit of the range) refer to a hydrocarbon chain (in the case of alkynylene, the chain links two moieties) containing one or more triple bond. Such groups as defined herein may be straight-chain or, when there is a sufficient number (i.e. a minimum of three or four, as appropriate) of carbon atoms, be branched-chain.

In the instance where a 'cycloalkyl' group (e.g. $C_{3-q}$ cycloalkyl) is specifically mentioned, such groups may be monocyclic or bicyclic non-aromatic alkyl groups, which may further be bridged (so forming, for example, fused ring systems). Such cycloalkyl groups may be saturated or unsaturated, e.g. containing one or more double bond (forming for example a $C_{5-q}$ cycloalkenyl). Optional substituents may be attached at any point on the cycloalkyl group. Cycloalkyl groups that may be mentioned preferably include $C_{3-12}$ cycloalkyl, for instance a 3- to 7-membered monocyclic cycloalkyl group, a $C_{7-11}$ (e.g. $C_{8-11}$) bicyclic cycloalkyl group or a $C_{8-12}$ (e.g. $C_{9-11}$) tricyclic cycloalkyl group. As stated above, cycloalkyl groups may further be bridged, so forming, for example, an adamantyl group (for example when a bicyclic cycloalkyl group is bridged). The term 'acyclic' alkyl group when used herein refers to an alkyl group that is not cyclic, but may be branched-chain or, is preferably, straight-chain.

For the avoidance of doubt, the term "bicyclic", when employed in the context of cycloalkyl, refers to such groups in which the second ring is formed between two adjacent atoms of the first ring (i.e. systems of two rings share one bond formed with two adjacent carbon atoms). The term "bridged", when employed in the context of cycloalkyl groups refers to monocyclic or bicyclic groups in which two non-adjacent atoms are linked by an alkylene chain.

The term "halo", when used herein, includes fluoro, chloro, bromo and iodo.

Aryl groups that may be mentioned include $C_{6-14}$ (e.g. $C_{6-10}$) aryl groups. Such groups may be monocyclic, bicyclic or tricyclic and have between 6 and 14 ring carbon atoms, in which at least one ring is aromatic. $C_{6-14}$ aryl groups include phenyl, naphthyl and the like, such as 1,2,3,4-tetrahydronaphthyl, indanyl, indenyl and fluorenyl. The point of attachment of aryl groups may be via any atom of the ring system, for instance when aryl groups are bicyclic or tricyclic, they are linked to the rest of the molecule via an atom of an aromatic or non-aromatic ring.

Heteroaryl groups that may be mentioned include those which have between 5 and 14 (e.g. 10) members. Such groups may be monocyclic, bicyclic or tricyclic, provided that at least one of the rings is aromatic and wherein at least one (e.g. one to four) of the atoms in the ring system is other than carbon (i.e. a heteroatom). Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothiadiazolyl (including 2,1,3-benzothiadiazolyl), benzothienyl, carbazolyl, chromanyl, cinnolinyl, furanyl, imidazolyl, imidazopyridyl (including imidazo[4,5-b]pyridyl, imidazo[5,4-b]-pyridyl and imidazo[1,2-a]pyridyl), indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,3,4-oxadiazolyl), oxazolyl, phenazinyl, phenothiazinyl, phthalazinyl, pteridinyl, purinyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydro-isoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,3,4-thiadiazolyl), thiazolyl, oxazolopyridyl (including oxazolo[4,5-b]pyridyl, oxazolo[5,4-b]pyridyl and, in particular, oxazolo[4,5-c]pyridyl and oxazolo[5,4-c]pyridyl), thiazolopyridyl (including thiazolo[4,5-b]pyridyl, thiazolo[5,4-b]pyridyl and, in particular, thiazolo[4,5-c]pyridyl and thiazolo[5,4-c]pyridyl), thiochromanyl, thienyl, triazolyl (including 1,2,3-triazolyl and 1,2,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. When heteroaryl groups are bicyclic or tricyclic, they may be linked to the rest of the molecule via an atom of an aromatic or non-aromatic ring. Heteroaryl groups may also be in the N— or S— oxidised form (so forming, for example, a pyridine N-oxide).

Heterocycloalkyl groups that may be mentioned include non-aromatic monocyclic and bicyclic heterocycloalkyl groups (which groups may further be bridged) in which at least one (e.g. one to four) of the atoms in the ring system is other than carbon (i.e. a heteroatom), and in which the total number of atoms in the ring system is between three and twelve (e.g. between five and ten). Further, such heterocycloalkyl groups may be saturated or unsaturated containing one or more double and/or triple bonds, forming for example a $C_{2-q}$ heterocycloalkenyl (where q is the upper limit of the range) or a $C_{7-q}$ heterocycloalkynyl group. $C_{2-q}$ heterocycloalkyl groups that may be mentioned include 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom.

Further, in the case where the substituent is another cyclic compound, then the cyclic compound may be attached through a single atom on the heterocycloalkyl group, forming a so-called "spiro"-compound. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N— or S— oxidised form.

Heteroatoms that may be mentioned include phosphorus, silicon, boron, tellurium, selenium and, preferably, oxygen, nitrogen and sulfur.

For the avoidance of doubt, in cases in which the identity of two or more substituents in a compound of formula I may be the same, the actual identities of the respective substituents are not in any way interdependent. For example, in case of $R^8$, the respective —$C(R^8)$— groups in question may be the same or different. Similarly, when groups are substituted by more than one substituent as defined herein, the identities of those individual substituents are not to be regarded as being interdependent. For example, when an A group is substituted by two $R^9$ substituents, in which, in both cases, $R^9$ represents $C_{1-7}$ alkyl substituted by —$N(R^{y1})R^{y2}$, then the identities of the two —$N(R^{y1})R^{y2}$ groups are not to be regarded as being interdependent, i.e. the two —$N(R^{y1})R^{y2}$ moieties may be the same or different, i.e. at each occurrence, $R^{y1}$ and $R^{y2}$ may also be the same or different.

For the avoidance of doubt, when a term such as "$R^{y1}$ to $R^{y15}$" is employed herein, this will be understood by the skilled person to mean $R^{y1}$, $R^{y2}$, $R^{y3}$, $R^{y4}$, $R^{y5}$, $R^{y6}$, $R^{y7}$, $R^{y8}$, $R^{y9}$, $R^{y10}$, $R^{y11}$, $R^{y12}$, $R^{y13}$, $R^{y14}$, and $R^{y15}$ inclusively. Further, when a term such as "$R^1$ to $R^5$" is employed herein, the skilled person will understand this to mean $R^1$, $R^2$, $R^3$, $R^{3a}$, $R^4$ and $R^5$ inclusively. Similarly, when the term "$Q^2$ to $Q^4$" is employed, this will be understood to mean $Q^2$, $Q^3$, $Q^{3a}$ and $Q^4$ inclusively.

For the avoidance of doubt, when the compound of formula I is substituted by a heterocycloalkyl or heteroaryl group, for example when $R^1$ or $R^8$ represent such substituents, then the point of attachment may be via a carbon atom or heteroatom (e.g. nitrogen heteroatom), assuming that the valency of the heteroatom permits. Similarly, when heterocycloalkyl or heteroaryl groups are substituted with further substituents, then those substituents may be attached at any position including on a carbon atom or heteroatom (e.g. a nitrogen heteroatom), again assuming that the valency permits.

For the avoidance of doubt, where it is mentioned herein that alkyl, alkenyl, alkynyl or cycloalkyl groups may be substituted with one or more halo atoms, then those halo atoms are preferably fluoro atoms.

The skilled person will appreciate that there may be free rotation around the nitrogen-carbon bond to which the requisite phenyl ring bearing the $R^1$ to $R^4$ substituents is pending. In view of this (when $Q^2$ to $Q^4$ respectively represent —$C(R^2)$=, —$C(R^3)$=, —$C(R^{3a})$= and —$C(R^4)$=), the $R^1$ and $R^2$ positions are 'identical' (as are the $R^3$ and $R^{3a}$ positions) relative to the point of attachment of that phenyl ring. Hence, the definitions of $R^1$ and $R^2$ may be interchanged (in which case the definitions of $R^3$ and $R^{3a}$ are also 'interchanged', relative to the definitions of $R^1$ and $R^2$), in view of the fact that both $R^1$ and $R^2$ represent ortho phenyl substituents. The important aspect in relation to the $R^1$ to $R^4$ substituents is therefore their positions relative to one another, rather than their positions relative to the point of attachment of that phenyl ring to the rest of the compound of formula I. For the avoidance of doubt, when preferred features are mentioned herein, then such features may be taken independently of others preferred features or conjunctively with other preferred features.

The skilled person will appreciate that compounds of formula I that are the subject of this invention include those that are stable. That is, compounds of the invention include those that are sufficiently robust to survive isolation from e.g. a reaction mixture to a useful degree of purity.

In one embodiment, the invention provides compounds of formula I as described above and in which
$Q^2$ represents —C($R^2$)═; and
$Q^3$, $Q^{3a}$ and $Q^4$ respectively represent —C($R^3$)═, —C($R^{3a}$)═ and —C($R^4$)═;
or
any one $Q^3$, $Q^{3a}$ and $Q^4$ may alternatively and independently represent —N═;

In another embodiment, the invention provides compounds of formula I according to any of the preceding embodiments and in which
$Q^2$, $Q^3$ and $Q^{3a}$ respectively represent —C($R^2$)═, —C($R^3$)═ and —C($R^{3a}$)═; and
$Q^4$ represents —N═.

In another embodiment, the invention provides compounds of formula I according to any of the preceding embodiments and
in which
$Q^2$, $Q^{3a}$ and $Q^4$ respectively represent —C($R^2$)═, —C($R^{3a}$)═ and —C($R^4$)═; and
$Q^3$ represents —N═;
or
$Q^2$, $Q^3$ and $Q^4$ respectively represent —C($R^2$)═, —C($R^3$)═ and —C($R^4$)═; and
$Q^a$ represents —N═.

In another embodiment, the invention provides compounds of formula I according to any of the preceding embodiments and
in which
$R^1$ represents $C_{1-4}$ alkyl (optionally substituted by one or more fluoro atoms), $C_{3-6}$ cycloalkyl or halo.

In another embodiment, the invention provides compounds of formula I according to any of the preceding embodiments and
in which
$R^1$ represents $C_{1-3}$ alkyl (optionally substituted by one or more fluoro atoms), $C_{3-6}$ cycloalkyl or halo.

In another embodiment, the invention provides compounds of formula I according to any of the preceding embodiments and
in which
$R^2$ represents hydrogen, $C_{1-4}$ alkyl [optionally substituted by one or more atoms selected from fluoro, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, S(O)$_2$N($R^{y13}$)$R^{y14}$ and —C(O)$R^{y15}$], $C_{3-6}$ cycloalkyl, halo or —O—$C_{1-3}$ alkyl (optionally substituted by one or more fluoro atoms).

In another embodiment, the invention provides compounds of formula I according to any of the preceding embodiments and
in which
$R^2$ represents hydrogen, $C_{1-3}$ alkyl [optionally substituted by one or more atoms selected from fluoro, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)—$R^{y11}$, —S(O)$_2$O—$R^{y12}$, S(O)$_2$N($R^{y13}$)$R^{y14}$ and —C(O)$R^{y15}$], $C_{3-6}$ cycloalkyl, halo or —O—$C_{1-3}$ alkyl (optionally substituted by one or more fluoro atoms).

In another embodiment, the invention provides compounds of formula I according to any of the preceding embodiments and
in which
$R^3$, $R^{3a}$ and $R^4$ independently represent hydrogen, $C_{1-3}$ alkyl (optionally substituted by one or more fluoro atoms) or halo.

In another embodiment, the invention provides compounds of formula I according to any of the preceding embodiments and
in which
$R^9$ represents halo, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$ and/or —C(O)$R^{y15}$; or
$C_{1-7}$ alkyl optionally substituted by one or more substituents selected from fluoro, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$ and/or —C(O)$R^{y15}$; or
aryl, heteroaryl (which latter two groups are optionally substituted by one or more substituents selected from —O—$C_{1-3}$ alkyl, —CN, halo and $C_{1-2}$ alkyl optionally substituted by one or more fluoro atoms); or any two $R^9$ groups may be linked together as defined above.

In another embodiment, the invention provides compounds of formula I according to any of the preceding embodiments and
in which
$R^8$ represents hydrogen, halo, $C_{1-3}$ alkyl [optionally substituted by one or more substituents selected from fluoro, —O$R^{y10}$, —N($R^{y1}$), $R^{y2}$, —N($R^{y3}$)—C(O)—$R^{y4}$, and —C(O)N($R^{y8}$)$R^{y9}$] or —O$R^{y10}$.

In another embodiment, the invention provides compounds of formula I according to any of the preceding embodiments and
in which
$R^6$ represents hydrogen or $C_{1-6}$ alkyl optionally substituted by one or more substituents selected from —N($R^{y1}$)$R^{y2}$, —N($R^{y3}$)—C(O)—$R^{y4}$, —N($R^{y6}$)—S(O)$_2$—$R^{y6}$, —C(O)O$R^{y7}$, —C(O)N($R^{y8}$)$R^{y9}$, —O$R^{y10}$, —S(O)$_2$$R^{y11}$ and a 4- to 6-membered heterocycloalkyl group (containing two or one heteroatom(s) selected from oxygen and nitrogen).

In another embodiment, the invention provides compounds of formula I according to any of the preceding embodiments and
in which
$R^{x2}$, $R^{y1}$, $R^{y2}$, $R^{y3}$, $R^{y5}$, $R^{y7}$, $R^{y8}$, $R^{y9}$, $R^{y10}$, $R^{y12}$, $R^{y13}$, and $R^{y14}$ independently represent hydrogen or $C_{1-4}$ alkyl optionally substituted by one or more fluoro atoms or —O$C_{1-2}$ alkyl groups; or any pair of $R^{y1}$ and IV, $R^{y8}$ and $R^{y9}$ and/or $R^{y13}$ and $R^{y14}$ are linked together to form a 3- to 7-membered ring, optionally containing one further nitrogen or oxygen heteroatom, one or two further double bonds, and which ring is optionally substituted by one or more $C_{1-2}$ alkyl or ═O substituents.

In another embodiment, the invention provides compounds of formula I according to any of the preceding embodiments and in which $R^{y4}$, $R^{y6}$, $R^{y11}$ and $R^{y16}$ independently represent $C_{1-4}$ alkyl.

In another embodiment, the invention provides compounds of formula I according to any of the preceding embodiments and in which A represents $C_{1-12}$ linear or branched alkyl, aryl, heteroaryl, 5- or 6-membered heterocycloalkyl; or $C_{3-10}$ cycloalkyl, all of which groups are optionally substituted by one or more substituents selected from $R^9$.

In another embodiment, the invention provides compounds of formula I according to any of the preceding embodiments and in which A represents $C_{4-12}$ linear or branched alkyl, aryl, heteroaryl, 5- or 6-membered heterocycloalkyl; or $C_{3-7}$ cycloalkyl (all of which groups are optionally substituted by one or more substituents selected from $R^9$); or arylmethylene, heteroarylmethylene [which latter two groups are optionally substituted by one or more groups selected from $C_{1-7}$ alkyl (optionally substituted by one or more substituents selected from fluoro and —$OR^{x2}$), halo, —CN and/or —O—$C_{1-7}$ alkyl (optionally substituted by one or more fluoro atoms)].

In another embodiment, the invention provides compounds according to any of the preceding embodiments, namely compounds of formula Ia, Ib, Ic or Id

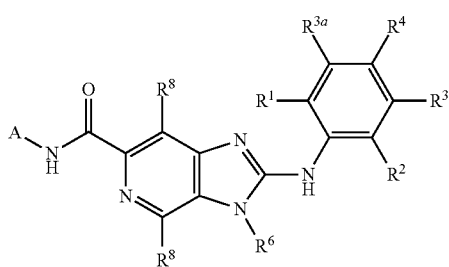

Ia

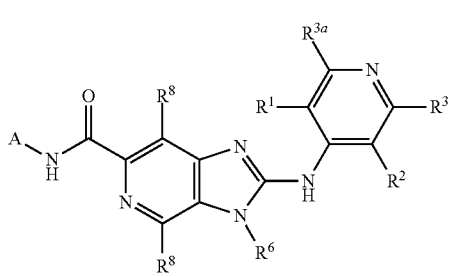

Ib

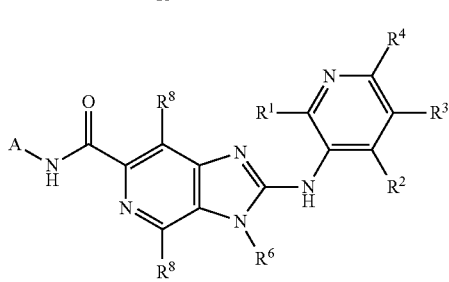

Ic

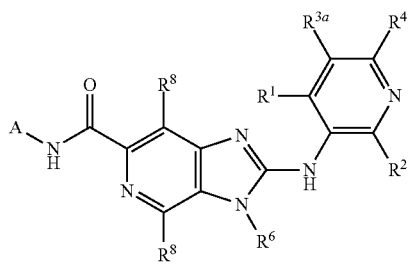

Id in which $R^1$ represents $C_{1-3}$ alkyl (optionally substituted by one or more fluoro atoms), $C_{3-6}$ cycloalkyl, fluoro, chloro, bromo;

$R^2$ represents hydrogen, $C_{1-3}$ alkyl (optionally substituted by one or more fluoro atoms), $C_{3-6}$ cycloalkyl, fluoro, chloro, bromo;

$R^3$, $R^{3a}$ and $R^4$ independently represent hydrogen, fluoro, chloro, bromo, $C_{1-3}$ alkyl (optionally substituted by one or more fluoro atoms);

$R^6$ represents hydrogen or $C_{1-6}$ alkyl optionally substituted by one or more substituents selected from fluoro, —N($R^{y1}$)$R^{y2}$—N($R^{y3}$)—C(O)—$R^{y4}$, —N($R^{y6}$)—S(O)$_2$—$R^{y6}$, —C(O)$OR^{y7}$, —C(O)N($R^{y8}$)$R^{y9}$, —$OR^{y10}$, —S(O)$_2$$R^{y11}$ and a 4- to 6-membered heterocycloalkyl group (containing two or one heteroatom(s) selected from oxygen and nitrogen);

$R^8$ independently represents hydrogen, fluoro, chloro, bromo, —$OR^{y10}$ or $C_{1-3}$ alkyl (optionally substituted by one or more fluoro atoms);

A represents phenyl, pyridyl, 5- or 6-membered heterocycloalkyl, $C_{3-7}$ cycloalkyl, $C_{5-8}$ linear or branched alkyl (all of which groups are optionally substituted by one or more substituents selected from $R^9$), or benzyl, pyridylmethylene [which latter two groups are optionally substituted by one or more groups selected from $C_{1-7}$ alkyl (optionally substituted by one or more substituents selected from fluoro and —$OR^{x2}$), halo, —CN and/or —O—$C_{1-7}$ alkyl (optionally substituted by one or more fluoro atoms)];

$R^9$ represents on each occasion when used herein: halo, —CN, —N($R^{y1}$)$R^{y2}$, —N($R^{y3}$)—C(O)—$R^{y4}$, —N($R^{y5}$)—S(O)$_2$—$R^{y6}$, —C(O)$OR^{y7}$, —C(O)N($R^{y8}$)$R^{y9}$, —$OR^{y10}$, —S(O)$_m$—$R^{y11}$, —S(O)$_2$O—$R^{y12}$, —S(O)$_2$N($R^{y13}$)$R^{y14}$ and/or —C(O)$R^{y15}$, $C_{1-6}$ alkyl optionally substituted by one or more substituents selected from halo, —CN, —N($R^{y1}$)$R^{y2}$, —N($R^{y3}$)—C(O)—$R^{y4}$, —N($R^{y5}$)—S(O)$_2$—$R^{y6}$, —C(O)$OR^{y7}$, —C(O)N($R^{y8}$)$R^{y9}$, —$OR^{y10}$, —S(O)$_m$—$R^{y11}$, —S(O)$_2$O—$R^{y12}$, —S(O)$_2$N($R^{y13}$)$R^{y14}$ and/or —C(O)$R^{y15}$;

or any two $R^9$ substituents, when attached to the adjacent atoms of the A group and, in the case where the $R^9$ substituents are attached to a non-aromatic A group, when attached to the same atoms, may be linked together to form, together with the essential atoms of the A group to which the relevant $R^9$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or =O substituents;

and
the substituents $R^{x2}$, $R^{y1}$, $R^{y2}$, $R^{y3}$, $R^{y4}$, $R^{y5}$, $R^{y6}$, $R^{y7}$, $R^{y8}$, $R^{y9}$, $R^{y10}$, $R^{y11}$, $R^{y12}$, $R^{y13}$, $R^{y14}$ and $R^{y15}$ have the meaning as defined in the embodiments above.

In another embodiment, the invention provides compounds according to any of the preceding embodiments, namely compounds of formula Ie, If, Ig or Ih

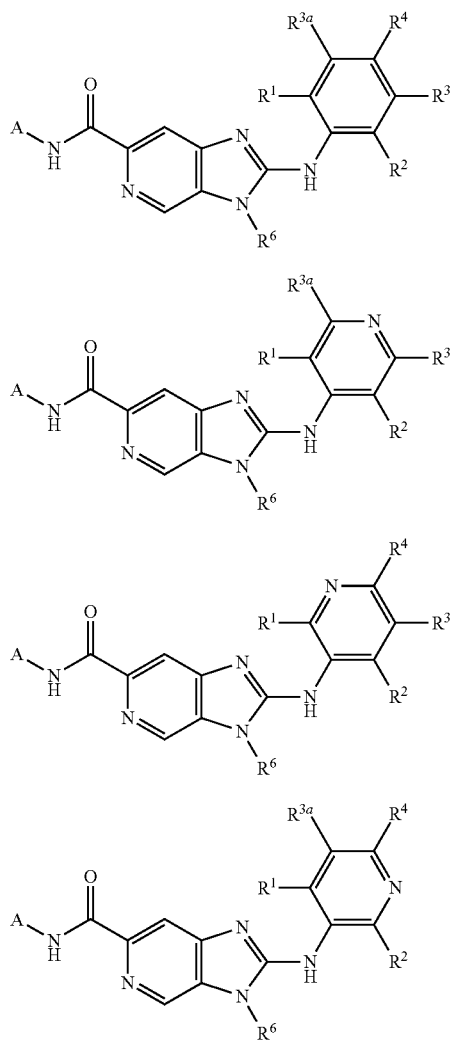

in which
$R^1$ represents chloro, bromo, fluoro, $C_{1-3}$ alkyl (which latter alkyl group is optionally substituted by one or more fluoro-atoms);
$R^2$ represents hydrogen, chloro, bromo, fluoro, $C_{1-3}$-alkyl (which latter alkyl group is optionally substituted by one or more fluoro atoms);
$R^3$, $R^{3a}$ and $R^4$ independently represent hydrogen, chloro, bromo, fluoro, $C_{1-3}$-alkyl (which latter alkyl group is optionally substituted by one or more fluoro atoms);
$R^6$ represents hydrogen; $C_{1-4}$ alkyl optionally substituted by one or more fluoro atoms;
A represents phenyl, 2-pyridyl, 5- or 6-membered heterocycloalkyl, $C_{3-7}$ cycloalkyl, $C_{5-8}$ linear or branched alkyl (all of which groups are optionally substituted by one or more substituents selected from $R^9$); or
benzyl, pyridin-2-yl-methylene [which latter two groups are optionally substituted by one or more groups selected from $C_{1-7}$ alkyl (optionally substituted by one or more substituents selected from fluoro and —$OR^{x2}$), halo, —CN and/or —O—$C_{1-7}$ alkyl (optionally substituted by one or more fluoro atoms)];
$R^9$ represents halo, —O—$C_{1-4}$ alkyl, $C_{1-4}$ alkyl, $C_{3-5}$ cycloalkyl, (which latter three groups are optionally substituted by one or more fluoro atoms.

In a further embodiment, the invention provides compounds namely those of the examples described hereinafter.

Compounds of the invention may be made in accordance with techniques that are well known to those skilled in the art, for example as described hereinafter.

According to a further aspect of the invention there is provided a process for the preparation of a compound of formula I, which process comprises:
(i) for compounds of formula I, reaction of a compound of formula II,

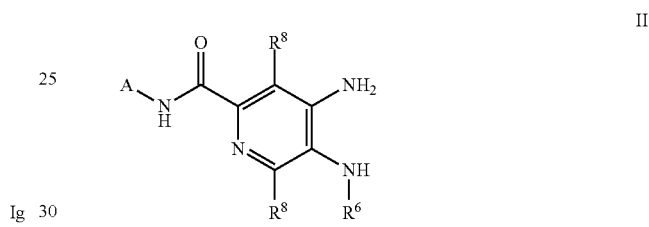

wherein: in each case, $R^6$, $R^8$ and A are as hereinbefore defined, with a compound of formula III,

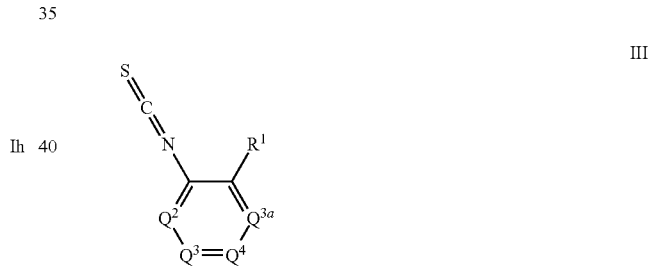

wherein $R^1$, $Q^2$, $Q^3$, $Q^{3a}$ and $Q^4$ are as hereinbefore defined, under standard conditions known to those skilled in the art, for example in the presence of a suitable solvent (such as diethyl ether, or, preferably, dimethylformamide, dichloromethane, acetonitrile and/or tetrahydrofuran) and preferably in the presence of a suitable 'coupling' reagent (which reagent is preferably added during the course of the reaction, e.g. when there is no more starting material present and/or a thiourea intermediate has been formed) that may enhance the reactivity of any intermediate that may be formed (e.g. a thiourea intermediate such of formulae IIIA, IIIB, IIIC and/or IIID described hereinafter) between the reaction of the compound of formula II with the compound of formula III, for instance a carbodiimide based compound such as dicyclohexylcarbodiimide (DCC), 1-ethyl-3-(3-dimethylaminopropyl) carbodiimide (or salt, e.g. hydrochloride, thereof) or, preferably N,N-diisopropylcarbodiimide (DIC), which reaction may proceed at any suitable temperature (e.g. one between about 0° C. to about 200° C.), and which may also be performed in the presence of an additive (such as 2,2,2-trifluoro-N,O-bis-(trimethylsilyl)-acetamide).

Alternatively, this reaction may be performed in the presence of a suitable base or mixture of bases, such as those described hereinafter (process step (ii)), for example by reaction in the presence of triethylamine and/or DMAP (optionally in the presence of a suitable solvent such as dichloromethane), after which any intermediate so formed may be protected, optionally isolated and reacted in the presence of an aqueous basic solution (e.g. aqueous NaOH; optionally mixed with a further suitable solvent such as an alcoholic solvent), which reaction may take place at ambient temperature or up to reflux. The skilled person will appreciate that the reaction between compounds of formulae II and III may proceed via intermediates of formulae IIIA or III B (as appropriate),

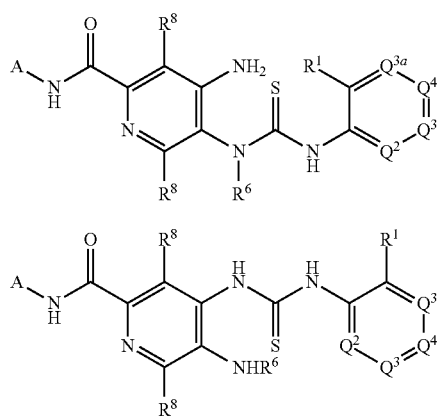

wherein $R^1$, $R^6$, $R^8$, $Q^2$, $Q^3$, $Q^{3a}$, $Q^4$ and A are as hereinbefore defined. Such intermediates may be isolated or may be produced in situ in the reaction to form a compound of formula I. When such intermediates are produced separately, then they may be reacted in the presence of solvent (e.g. acetonitrile and/or methanol) and that the intermediate so formed may be then reacted under the conditions set out above;

(ii) for compounds of formula I, reaction of a compound of formula IV,

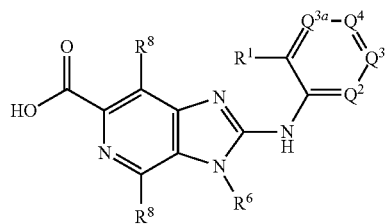

or a derivative thereof (e.g. an ester derivative, such as a methyl ester), wherein $R^1$, $Q^2$, $Q^3$, $Q^{3a}$, $Q^4$, $R^6$ and $R^8$ are as hereinbefore defined, with a compound of formula V,

A-NH$_2$     V wherein A is as hereinbefore defined, under coupling reaction conditions, for example at around room temperature or above (e.g. up to 40-180° C.), optionally in the presence of a suitable base (e.g. sodium hydride, sodium bicarbonate, potassium carbonate, pyrrolidino-pyridine, pyridine, triethylamine, tributylamine, trimethylamine, dimethylaminopyridine, diisopropylamine, 1,8-diazabicyclo[5.4.0]undec-7-ene, sodium hydroxide, N-ethyldiisopropylamine, N-(methylpolystyrene)-4-(methylamino)pyridine, butyllithium (e.g. n-, s- or t-butyllithium) or mixtures thereof), an appropriate solvent (e.g. tetrahydrofuran, pyridine, toluene, dichloromethane, chloroform, acetonitrile, dimethylformamide, dimethylsulfoxide, trifluoromethylbenzene, triethylamine or water) and a suitable coupling agent (e.g. 1,1'-carbonyldiimidazole, N,N'-dicyclohexylcarbodiimide, N,N-diisopropylcarbodiimide, 1-(3-dimethylamino-propyl)-3-ethylcarbodiimide (or salt, e.g. hydrochloride thereof), N,N'-disuccinimidyl carbonate, benzotriazol-1-yloxytris (dimethylamino) phosphonium hexafluoro-phosphate, 2-(1H-benzotriazol-1-yl)-1,1,3,3-tetramethyluronium hexafluorophosphate, benzotriazol-1-yloxytrispyrrolidino-phosphonium hexafluorophosphate, bromo-tris-pyrrolidino-phosphonium hexafluorophosphate, 2-(1H-benzotriazol-1-yl)-1,1,3,3-tetramethyluronium tetrafluorocarbonate, 1-cyclohexyl-carbodiimide-3-propyloxymethyl polystyrene, O-(7-aza-benzotriazol-1-yl)-N,N,N',N'-tetra-methyluronium hexafluorophosphate, O-pentafluorophenyl-N,N,N',N'-tetra-methyluronium hexafluorophosphate, O-(benzotriazol-1-yl)-N,N,N',N'-tetra-methyluronium tetrafluoroborate or mixtures thereof). Alternatively, compounds of formula III may first be activated by treatment with a suitable reagent (e.g. oxalyl chloride, thionyl chloride, phosphorous pentachloride, phosphorous oxychloride, (1-chloro-2-methyl-propen-yl)-dimethyl-amine or the like, or mixtures thereof) optionally in the presence of an appropriate solvent (e.g. dichloromethane, THF, toluene or benzene) and a suitable catalyst (e.g. DMF), resulting in the formation of the respective acyl chloride. This activated intermediate may then be reacted with a compound of formula V under standard conditions, such as those described above. An alternative way of performing this step, includes the reaction of an ester derivative of a compound of formula IV (e.g. an ethyl or, preferably, a methyl ester) with a compound of formula V, in the presence of, e.g. trimethylaluminium, optionally in the presence of a suitable solvent (e.g. dichloromethane or tetrahydrofuran) under an inert atmosphere;

Compounds of formula II may be prepared by reduction of a compound of formula XX,

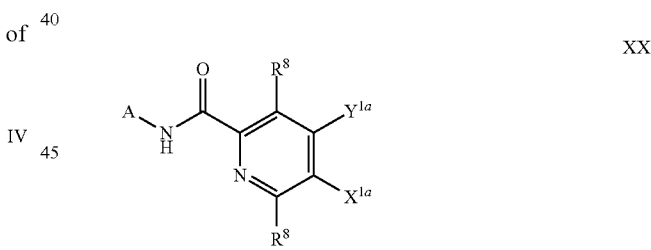

wherein $Y^{1a}$ represents —NO$_2$ (or an azido group), and $X^{1a}$ represents —N(R$^6$)H or, in the case where the compound of formula II to be formed is one in which both $X^1$ and $Y^1$ represent —N(H)—, then both of $X^{1a}$ and $Y^{1a}$ may represent —NC$_2$ (or an azido group), and $R^8$ and A are as hereinbefore defined, under standard conditions known to those skilled in the art, for example, under hydrogenation reaction conditions, including catalytic hydrogenation reaction conditions (e.g. employing a precious metal catalyst such as a platinum group catalyst, e.g. platinum or, preferably, palladium, which latter may be employed as 10%-20% Pd/C, or employing a non-precious metal catalyst such as one based on nickel, e.g. Raney nickel), for example in the presence of a suitable solvent such as diethyl ether or, preferably, ethyl acetate, tetrahydrofuran or an alcoholic solvent (e.g. EtOH or MeOH), or mixtures thereof. Alternatively, the reduction may be performed in the presence of other suitable conditions, such as employing a mixture of Sn/HCl or Fe powder in EtOH and/or acetic acid and NH$_4$Cl.

Compounds of formula IIIA and IIIB (the latter with $R^6$=H) may be prepared by reduction of a corresponding compound of formula XXA or XXB,

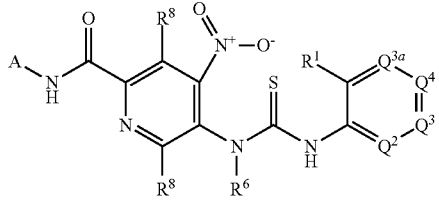
XXA

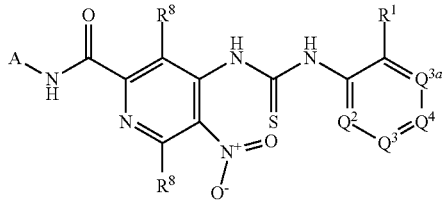
XXB wherein $R^1$, $R^6$, $R^8$, $Q^2$, $Q^3$, $Q^{3a}$, $Q^4$ and A are as hereinbefore defined, under reduction reaction conditions for example such as those hereinbefore described in respect of preparation of compounds of formula II. The skilled person will appreciate that a similar reaction may be performed on compounds in which the nitro group is replaced with an azido group.

Compounds of formula XX may be prepared by nitration of a compound of formula XXIII,

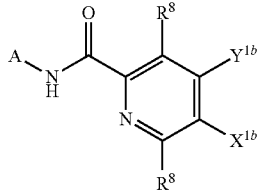
XXIII wherein $X^{1b}$ represents —N($R^6$)H and $Y^{1b}$ represents hydrogen, or $X^{1b}$ represents hydrogen and $Y^{1b}$ represents —NH$_2$, and $R^8$ and A are as hereinbefore defined, under standard nitration reaction conditions, for example in the presence of a mixture of nitric acid and sulfuric acid (e.g. conc. sulfuric acid) which may be mixed at low temperatures (e.g. at about 0° C.), thereby forming a nitronium ion in situ, which may then react with the compound of formula XXIII.

Alternatively, compounds of formula XX in which one of $X^{1a}$ and $Y^{1a}$ represents —NO$_2$ and the other represents —NH$_2$ or —N($R^6$)H may be prepared by reaction of a compound of formula XXIIIA,

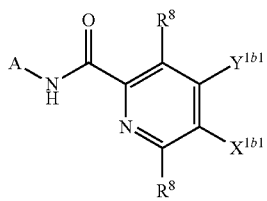
XXIIIA wherein one of $X^{1b1}$ and $Y^{1b1}$ represents —NO$_2$ and the other represents a suitable leaving group, such as hereinbefore defined in respect of $L^{yb}$ (and preferably represents a halo group, such as chloro), and A and $R^8$ are as hereinbefore defined, with either: ammonia (or a suitable source thereof; for example, methanolic ammonia, or the like); or, for the introduction of the appropriate —N($R^6$)H (e.g. when $R^6$ is hydrogen), the corresponding amine $R^6$—NH$_2$, under standard nucleophilic aromatic substitution reaction conditions.

Compounds of formula XXA and XXB in which $X^1$ and $Y^1$ preferably represent —N(H)— may be prepared by reaction of a compound of formula XXIIIB or XXIIIC,

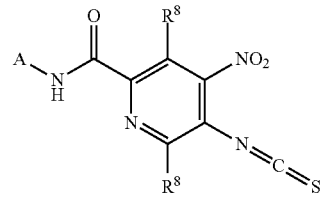
XXIIIB

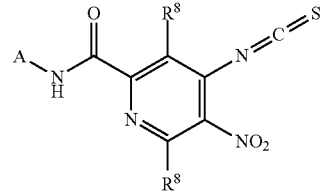
XXIIIC respectively, wherein $R^8$ and A are as hereinbefore defined, with a compound of formula X as hereinbefore defined, under standard reaction conditions, for example such as those hereinbefore described in respect of preparation of compounds of formula I (process step (iv) above).

Compounds of formulae III, IIIA, IIIB, IV, V, VI, VII, VIII, X, XI, XII, XIII, XIV, XV, XVII, XVIII, XIX, XXIIB, XXIIC, XXIII, XXIIIB, XXIIIC, XXIIIA, XXV, XXVI, XXVIA, XXVII and XXVIII are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991.

The substituents $R^1$, $Q^2$, $Q^3$, $Q^{3a}$, $Q^4$, $R^5$, $Z^1$, $Z^2$, $Z^3$, B, E, X, Y, L and A in final compounds of formula I or relevant intermediates may be modified one or more times, after or during the processes described above by way of methods that are well known to those skilled in the art. Examples of such methods include substitutions, reductions (e.g. of double bonds to single bonds by hydrogenation), oxidations, alkylations, acylations, hydrolyses, esterifications, etherifications and nitrations. The precursor groups can be changed to a different such group, or to the groups defined in formula I, at any time during the reaction sequence. In this respect, the skilled person may also refer to "*Comprehensive Organic Functional Group Transformations*" by A. R. Katritzky, O. Meth-Cohn and C. W. Rees, Pergamon Press, 1995.

For example, in the case where $R^1$ or $R^2$ represents a halo group, such groups may be inter-converted one or more times, after or during the processes described above for the preparation of compounds of formula I. Appropriate reagents include NiCl$_2$ (for the conversion to a chloro group). Further, oxidations that may be mentioned include oxidations of sulfanyl groups to sulfoxide and sulfonyl groups, for example employing standard reagents (e.g. meta-chloroperbenzoic acid, KMnO$_4$ or a solution of Oxone® in ethylenediaminetetraacetic acid).

Other transformations that may be mentioned include the conversion of a halo group (preferably iodo or bromo) to a —CN or 1-alkynyl group (e.g. by reaction with a compound which is a source of cyano anions (e.g. sodium, potassium, copper (I) or zinc cyanide) or with a 1-alkyne, as appropriate). The latter reaction may be performed in the presence of a suitable coupling catalyst (e.g. a palladium and/or a copper based catalyst) and a suitable base (e.g. a tri-(C$_{1-6}$ alkyl)amine such as triethylamine, tributylamine or ethyldiisopropylamine). Further, amino groups and hydroxy groups may be introduced in accordance with standard conditions using reagents known to those skilled in the art.

Compounds of formula I may be isolated from their reaction mixtures using conventional techniques.

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined but without the provisos for use as a pharmaceutical.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention. By "prodrug of a compound of the invention", we include compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds (e.g. compounds of the invention) that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity (e.g. similar or pronounced pharmacological activity as compared to the compounds of the invention from which they are formed).

Compounds of the invention are particularly useful because they may inhibit the activity of a member of the MAPEG family.

Compounds of the invention are particularly useful because they may inhibit (for example selectively) the activity of prostaglandin E synthases (and particularly microsomal prostaglandin E synthase-1 (mPGES-1)), i.e. they prevent the action of mPGES-1 or a complex of which the mPGES-1 enzyme forms a part, and/or may elicit a mPGES-1 modulating effect, for example as may be demonstrated in the test described below.

Compounds of the invention may thus be useful in the treatment of those conditions in which inhibition of a PGES, and particularly mPGES-1, is required.

Compounds of the invention are thus expected to be useful in the treatment of inflammation. Further, as the compounds of the invention may be of use as mPGES inhibitors (e.g. mPGES-1 inhibitors), they may also be useful in preventing or treating benign or malignant neoplasias (as they may reduce the production of PGE2). Hence, the compounds of the invention may also be useful in treating cancers.

The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions.

The term "inflammation" will thus also be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Accordingly, compounds of the invention may be useful in the treatment of asthma, chronic obstructive pulmonary disease, pulmonary fibrosis, inflammatory bowel disease, irritable bowel syndrome, inflammatory pain, fever, migraine, headache, low back pain, fibromyalgia, myofascial disorders, viral infections (e.g. influenza, common cold, herpes zoster, hepatitis C and AIDS), bacterial infections, fungal infections, dysmenorrhea, burns, surgical or dental procedures, malignancies (e.g. breast cancer, colon cancer, and prostate cancer), hyperprostaglandin E syndrome, classic Bartter syndrome, atherosclerosis, gout, arthritis, osteoarthritis, juvenile arthritis, rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, psoriasis, stroke, diabetes mellitus, neurodegenerative disorders such as Alzheimer's disease and multiple sclerosis, autoimmune diseases, allergic disorders, rhinitis, ulcers, coronary heart disease, sarcoidosis and any other disease with an inflammatory component.

Compounds of the invention may also have effects that are not linked to inflammatory mechanisms, such as in the reduction of bone loss in a subject. Conditions that may be mentioned in this regard include osteoporosis, osteoarthritis, Paget's disease and/or periodontal diseases. Compounds the invention may thus also be useful in increasing bone mineral density, as well as the reduction in incidence and/or healing of fractures, in subjects. Compounds of the invention are indicated both in the therapeutic and/or prophylactic treatment of the above-mentioned conditions.

According to a further aspect of the present invention, there is provided a method of treatment of a disease which is associated with, and/or which can be modulated by inhibition of, a member of the MAPEG family such as a PGES (e.g. mPGES-1), $LTC_4$ synthase and/or FLAP and/or a method of treatment of a disease in which inhibition of the activity of a member of the MAPEG family such as PGES (and particularly mPGES-1), $LTC_4$ synthase and/or FLAP is desired and/or required (e.g. inflammation), which method comprises administration of a therapeutically effective amount of a compound of the invention, as hereinbefore defined but without the provisos, to a patient suffering from, or susceptible to, such a condition.

"Patients" include mammalian (including human) patients.

The term "effective amount" refers to an amount of a compound, which confers a therapeutic effect on the treated patient. The effect may be objective (i.e. measurable by some test or marker) or subjective (i.e. the subject gives an indication of or feels an effect).

Compounds of the invention will normally be administered orally, intravenously, subcutaneously, buccally, rectally, dermally, nasally, tracheally, bronchially, sublingually, by any other parenteral route or via inhalation, in a pharmaceutically acceptable dosage form. Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, as hereinbefore defined but without the provisos, in admixture with a pharmaceutically acceptable adjuvant, diluent or carrier. Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The invention further provides a process for the preparation of a pharmaceutical formulation, as hereinbefore defined, which process comprises bringing into association a compound of the invention, as hereinbefore defined but without the provisos, or a pharmaceutically acceptable salt thereof with a pharmaceutically-acceptable adjuvant, diluent or carrier. Compounds of the invention may also be combined with other therapeutic agents that are useful in the treatment of inflammation (e.g. NSAIDs and coxibs).

According to a further aspect of the invention, there is provided a combination product comprising:
(A) a compound of the invention, as hereinbefore defined but without the provisos; and
(B) another therapeutic agent that is useful in the treatment of inflammation, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined but without the provisos, another therapeutic agent that is useful in the treatment of inflammation, and a pharmaceutically-acceptable adjuvant, diluent or carrier; and
(2) a kit of parts comprising components:
(a) a pharmaceutical formulation including a compound of the invention, as hereinbefore defined but without the provisos, in admixture with a pharmaceutically-acceptable adjuvant, diluent or carrier; and
(b) a pharmaceutical formulation including another therapeutic agent that is useful in the treatment of inflammation in admixture with a pharmaceutically-acceptable adjuvant, diluent or carrier,
which components (a) and (b) are each provided in a form that is suitable for administration in conjunction with the other.

The invention further provides a process for the preparation of a combination product as hereinbefore defined, which process comprises bringing into association a compound of the invention as hereinbefore defined but without the provisos with another therapeutic agent that is useful in the treatment of inflammation, and a pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Compounds of the invention may be administered at varying doses. Oral, pulmonary and topical dosages may range from between about 0.01 mg/kg of body weight per day (mg/kg/day) to about 100 mg/kg/day, preferably about 0.01 to about 100 mg/kg/day, and more preferably about 0.1 to about 25 mg/kg/day. For e.g. oral administration, the compositions typically contain between about 0.01 mg to about 5000 mg, and preferably between about 1 mg to about 2000 mg, of the active ingredient. Intravenously, the most preferred doses will range from about 0.001 to about 10 mg/kg/hour during constant rate infusion. Advantageously, compounds may be administered in a single daily dose, or the total daily dosage may be administered in divided doses of two, three or four times daily. In any event, the physician, or the skilled person, will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

Compounds of the invention may have the advantage that they are effective, and preferably selective, inhibitors of a member of MAPEG family, e.g. inhibitors of prostaglandin E synthases (PGES) and particularly microsomal prostaglandin E synthase-1 (mPGES-1). The compounds of the invention may reduce the formation of the specific arachidonic acid metabolite $PGE_2$ without reducing the formation of other COX generated arachidonic acid metabolites, and thus may not give rise to the associated side-effects mentioned hereinbefore.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Biological Test

Microsomes from Rosetta *E. coli* bacteria expressing recombinant human mPGES-1 is dissolved in 0.1 M $KP_i$ pH 7.4 buffer containing 2.5 mM GSH. 50 µl of the enzyme is subsequently dispensed in a 384-well plate. 0.5 µl of the inhibitor dissolved in DMSO at is thereafter added to each well and incubated for 25 minutes at room temperature.

Subsequently, 2 µl of PGH2 dissolved in an appropriate solvent is added to each well and after one minute the acidified stop solution containing $FeCl_2$ is added. 4 µl of the total volume is transferred to a separate plate and diluted 750-fold in two separate steps before HTRF detection of PGE2.

The HTRf detection is performed by the use of a commercially available kit from CisBio essentially according to the manufacturer's protocol. Briefly, 10 µl of the diluted sample is transferred to a white 384-well plate. 5 µl of d2 and 5 µl Eu3+-Cryptate labeled anti-$PGE_2$ is added to each well containing samples by the use of a Multidrop. The plate is covered with a plastic self-adhesive film, centrifuged at 1200 rpm for 1 minute and subsequently stored at +4° C. over night.

After over night incubation the fluorescence is measured by the use of an appropriate microplate reader. The fluorescence of europium cryptate, and d2 are measured using the following excitation and emission wavelength, europium cryptate: $\lambda_{max}^{ex}=307$ nm, $\lambda_{max}^{em}=620$ nm and d2: $\lambda_{max}^{ex}=620$ nm, $\lambda_{max}^{em}=665$ nm), respectively. The extent of the specific FRET is measured as a ratio of the emission intensity at 665 nm vs. that at 620 nm. A standard curve using synthetic PGE2 is used to quantify the amount of PGE2 in unknown samples.

CHEMICAL EXAMPLES

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

| | |
|---|---|
| AIBN | Azo-bis-isobutyronitrile |
| aq. | aquaeous solution |
| Boc | tert.-butoxycarbonyl |
| DIC | diisopropyl-carbodiimide |
| DIPEA | N-ethyl-diisopropylamine |
| DMSO | dimethylsulphoxide |
| DMF | N,N-dimethylformamide |
| sat. | saturated |
| h | hour(s) |
| HATU | O-(7-azabenzotriazol-1-yl)-N,N,N',N'-tetramethyluronium-hexafluorophosphate |
| HBTU | O-Benzotriazole-1-yl-N,N,N',N'-tetramethyluronium-hexafluorophosphate |
| DPPA | Diphenylphosphoryl azide |
| HPLC | high performance liquid chromatography |
| i. vac. | in vacuo |
| conc. | concentrated |
| min | minute(s) |
| MS | mass spectrometry |
| NBS | N-bromo-succinimide |
| NMM | N-methyl-morpholine |
| NMP | N-methyl-pyrrolidin-2-one |
| o | ortho |
| PfTU | O-pentafluorophenyl-N,N,N',N'-tetramethyluronium-hexafluorophosphate |
| PPA | propanephosphonic acid cycloanhydride |
| quant. | quantitative |
| $R_f$ | retention factor |
| $R_t$ | retention time |
| mp | melting point |
| rac. | Racemic |
| M | mol/L |
| sat. | saturated |
| TBME | tert.-butyl-methyl-ether |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |
| tert. | tertiary |
| TLC | Thin layer chromatography |
| Σ | yield over all the steps carried out analogously as described |
| $KHCO_3$ | potassium-hydrogen-carbonate |
| $K_2CO_3$ | potassium carbonate |
| $Na_2SO_4$ | sodium sulfate |
| NaOH | sodium hydroxide |
| HCl | hydrochloric acid |
| DCC | N,N'-Dicyclohexylcarbodiimide |
| DIBAL-H | Diisobutylaluminium hydride |
| DMAP | 4-Dimethylaminopyridine |
| EDC | 3-(3-Dimethylaminopropyl)-1-ethyl-carbodiimide |
| EDCl | 3-(3-Dimethylaminopropyl)-1-ethyl-carbodiimide hydrochloride |

The HPLC/MS data, where specified, were obtained under the following conditions:

Agilent 1100 with quarternary pump, Gilson G215 Autosampler, HP diode array detector.

The following was used as the mobile phase:
E1: water with 0.15% formic acid
E2: acetonitrile
E3: water with 0.1% acetic acid Eluent Gradient A (Polar):

| time in min | % E1 | % E2 | flow rate in mL/min |
|---|---|---|---|
| 0.0 | 95 | 5 | 1.6 |
| 4.00 | 50 | 50 | 1.6 |
| 4.50 | 10 | 90 | 1.6 |
| 5.00 | 10 | 90 | 1.6 |
| 5.50 | 90 | 10 | 1.6 |

Eluent Gradient B (Standard):

| time in min | % E1 | % E2 | flow rate in mL/min |
|---|---|---|---|
| 0.0 | 95 | 5 | 1.6 |
| 4.50 | 10 | 90 | 1.6 |
| 5.00 | 10 | 90 | 1.6 |
| 5.50 | 90 | 10 | 1.6 |

Eluent Gradient C (Unpolar):

| time in min | % E1 | % E2 | flow rate in mL/min |
|---|---|---|---|
| 0.0 | 95 | 5 | 1.6 |
| 2.00 | 10 | 90 | 1.6 |
| 5.00 | 10 | 90 | 1.6 |
| 5.50 | 90 | 10 | 1.6 |

Eluent Gradient D (Ultrakurz-Polar):

| time in min | % E1 | % E2 | flow rate in mL/min |
|---|---|---|---|
| 0.0 | 95 | 5 | 1.6 |
| 2.00 | 50 | 50 | 1.6 |
| 2.25 | 10 | 90 | 1.6 |
| 2.5 | 10 | 90 | 1.6 |
| 2.75 | 95 | 5 | 1.6 |

Eluent Gradient E (Ultrakurz-Standard):

| time in min | % E1 | % E2 | flow rate in mL/min |
|---|---|---|---|
| 0.0 | 95 | 5 | 1.6 |
| 2.25 | 10 | 90 | 1.6 |
| 2.5 | 10 | 90 | 1.6 |
| 2.75 | 95 | 5 | 1.6 |

Eluent Gradient F (Ultrakurz-Unpolar):

| time in min | % E1 | % E2 | flow rate in mL/min |
|---|---|---|---|
| 0.0 | 95 | 5 | 1.6 |
| 1.00 | 10 | 90 | 1.6 |
| 2.5 | 10 | 90 | 1.6 |
| 2.75 | 95 | 5 | 1.6 |

Eluent Gradient G:

| time in min | % E3 | % E2 | flow rate in mL/min |
|---|---|---|---|
| 0.0 | 95 | 5 | 3 |
| 0.3 | 95 | 5 | 3 |
| 2 | 2 | 98 | 3 |
| 2.4 | 2 | 98 | 3 |
| 2.45 | 95 | 5 | 3 |
| 2.8 | 95 | 5 | 3 |

The following was used as the stationary phase: (column temperature: constant at 25° C.)
1: Zorbax StableBond C18, 3.5 μm, 4.6×75 mm
2: Waters Symmetry C18, 3.5 μm, 4.6×75 mm
3: Zorbax Bonus-RP C18, 3.5 μm, 4.6×75 mm
4: YMC-Pack ODS-AQ, 3 μm, 4.6×75 mm
5: XBridge C18, 3.5 μm, 4.6×75 mm
7: Zobrax Stable Bond C18, 1.8 μm, 3.0×30 mm
8: Sunfire C18, 2.5 μm, 3.0×30 mm
9: Xbridge C1, 2.5 μm, 3.0×30 mm
12: Zorbax Stable Bond C18, 3.5 μm, 4.6×75 mm The following was used as the stationary phase: (column temperature: constant at 20° C.)
10: Interchim Strategy C18, 5 μm, 4.6×50 mm
11: XRS C18, 5 μm, 4.6×50 mm The method is abbreviated using the above descriptions (eg. A1 for Eluent gradient A with stationary phase 1).

The diode array detection took place in a wavelength range from 210-550 nm

Range of mass-spectrometric detection: m/z 120 to m/z 1000

Alternatively, the following method was used, abbreviated CC:
HP1100 HPLC+DAD (Wavelength range: 210 nm to 500 nm), and Gilson 215 Autosampler RP-HPLC MS analyses were performed on a Waters ZQ2000 mass spectrometer The following was used as the mobile phase:
E1: water with 0.1% trifluoracetic acid
E2: acetonitrile with 0.1% trifluoracetic acid
Eluent Gradient:

| time in min | % E1 | % E2 | flow rate in mL/min |
|---|---|---|---|
| 0.0 | 95 | 5 | 1.5 |
| 2.00 | 0 | 100 | 1.5 |
| 2.50 | 0 | 100 | 1.5 |
| 2.60 | 95 | 5 | 1.5 |

The following was used as the stationary phase:
Sunfire C18 4.6×50 mm, 3.5 μm (column temperature: constant at 40° C.)

The diode array detection took place in a wavelength range from 210-500 nm

Range of mass-spectrometric detection: m/z 120 to m/z 820.

Alternatively, the following method was used, abbreviated EX1:
Column: Atlantis dC18 5 mm, 2.1×50 mm.
Mobile phase: 10-95% MeCN in 0.01% TFA.
Flow rate: 0.2 mL/min.
Detection: UV 254 nm.

Alternatively, the following method was used, abbreviated EX2:
Column: Acquity HPLC BEH SHIELD RP18 1.7 mm, 2.1×100 mm.
Mobile phase: 5-100% MeCN in 0.1% HCOOH.
Flow rate: 0.2 mL/min.
Detection: UV 254 nm/211 nm.

The following compounds are accompanied by structural drawings. The skilled person will appreciate that the rules of valency must be adhered to and hence there must be a certain number of bonds attached to each atom, which may not necessarily be depicted on the drawings. For example, in the case where a nitrogen heteroatom is depicted with only one or two bonds attached to it, the skilled person will realise that it should be attached to an additional one or two bonds (a total of three), in which such bonds are normally attached to one or two hydrogen atoms (so forming a —NH$_2$ or —N(H)— moiety).

Example 83

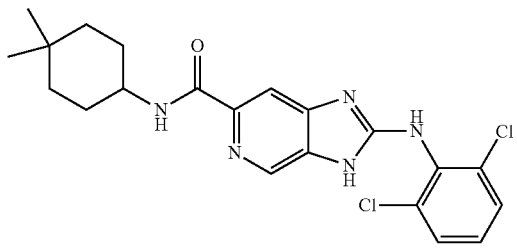 [SMILES: CC1(C)CCC(NC(=O)c2cc3nc(Nc4c(Cl)cccc4Cl)[nH]c3cn2)CC1]

2-(2,6-Dichloro-phenylamino)-3H-imidazo[4,5-c]pyridine-6-carboxylic acid (4,4-dimethyl-cyclohexyl)-amide

(83a) 4-Amino-pyridine-2-carboxylic acid (4,4-dimethyl-cyclohexyl)-amide

To a mixture of 4-amino-pyridine-6-carboxylic acid (250 mg, 1.81 mmol) with TBTU (600 mg, 1.87 mmol) and TEA (1 mL, 7.2 mmol) in 4 mL DMF was added 4,4-dimethyl-cyclohexylamine (300 mg, 1.83 mmol) and the mixture stirred at ambient temperature for 1 h. Then the mixture was poured into water at 0° C. and stirred for 5 min. The precipitate was filtered off, washed with water and dried at 55° C.
Yield: 340 mg (76%)
R$_t$ value: 2.38 min (B2)
Mass spectrum: (M+H)$^+$=248

(83b) 4-Nitramino-pyridine-2-carboxylic acid (4,4-dimethyl-cyclohexyl)-amide Fuming nitric acid (2.0 mL) was added to a mixture of the product obtained in 83a (340 mg, 1.38 mmol) and conc. sulphuric acid (4 mL) under cooling at 0° C. and stirred for 30 min at 0° C. The mixture was poured into water at 0° C. and adjusted to pH 2 by adding conc. ammonia. The mixture was filtrated, and the solid washed with water and dried overnight at ambient temperature.
Yield: 360 mg (90%); R$_t$ value: 4.20 min (B2); Mass spectrum: (M+H)$^+$=293

(83c) 4-Amino-5-nitro-pyridine-2-carboxylic acid (4,4-dimethyl-cyclohexyl)-amide The product obtained in 83b (360 mg, 1.23 mmol) was stirred at 85° C. in conc. sulphuric acid (5 mL) for 5 min. The mixture was poured into water at 0° C. and adjusted to pH 3-4 by adding conc. ammonia. The mixture was extracted with dichloromethane, the organic layers dried over MgSO$_4$ and concentrated i. vac. The residue was purified via HPLC (C-18 Symmetry, eluent-gradient: (water+0.15% HCOOH)/acetonitrile=90:10→0:100).
Yield: 100 mg (28%)
R$_t$ value: 4.46 min (B2)
C$_{14}$H$_{20}$N$_4$C$_3$ (292.33)
Mass spectrum: (M+H)$^+$=293

(83d) 4,5-Diamino-pyridine-2-carboxylic acid (4,4-dimethyl-cyclohexyl)-amide The product obtained in 83c (100 mg, 0.34 mmol) in 10 mL methanol was mixed with Raney nickel (25 mg) and hydrogenated at 3.4 bar for 2.5 h in a Parr apparatus. The mixture was filtered and the filtrate concentrated i. vac.
Yield: 80 mg (89%)
R$_t$ value: 2.47 min (B2)
Mass spectrum: (M+H)$^+$=263

(83e) 2-(2,6-Dichloro-phenylamino)-3H-imidazo[4,5-c]pyridine-6-carboxylic acid (4,4-dimethyl-cyclohexyl)-amide To the product obtained in 83d (75 mg, 0.29 mmol) in 4 mL DMF was added 1,3-dichloro-2-isocyanato-benzene and the mixture stirred at ambient temperature for 16 h. Then DIC (55 µL, 0.35 mmol) was added and the mixture stirred at ambient temperature for 20 h. 1 mL methanol was added and the product purified via RP-HPLC(C-18 symmetry; eluent-gradient: water+HCOOH/acetonitrile=90:10→0:100).
Yield: 28%
R$_t$ value: 3.58 min (C2)
Mass spectrum: (M+H)$^+$=432/434/436 (chlorine isotopes)
In analogy with the above described example, the following compounds were prepared:

| No. | Structural formula Name | Yield | Mass peak(s) | R$_f$ value or R$_t$ |
|---|---|---|---|---|
| 137 | 2-(2,6-Dichloro-phenylamino)-3H-imidazo[4,5-c]pyridine-6-carboxylic acid-cyclohexyl-amide | Σ: 6.7% | (M + H)+ = 404/406/408 (chlorine isotopes) | 2.13 min (C2) |

Example 360

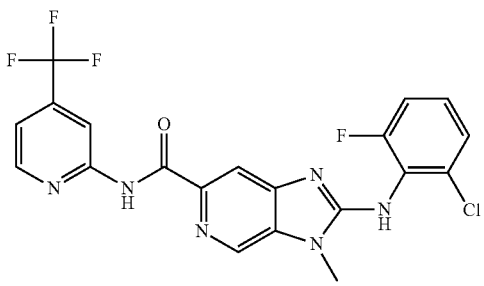 [SMILES: Cn1c(Nc2c(F)cccc2Cl)nc2cc(C(=O)Nc3cc(C(F)(F)F)ccn3)ncc21]

2-(2-Chloro-6-fluoro-phenylamino)-3-methyl-N-(4-trifluoromethyl-pyridin-2-yl)-3-H-imidazo[4,5-c]pyridine-6-carboxamide

(360a) 2-Bromo-5-fluoro-pyridine 1-oxide

2-Bromo-5-fluoropyridine (15 g, 85.6 mmol), trifluoroacetic acid (70 mL, 908 mmol) and hydrogen peroxide (35% in water) (9 mL, 105 mmol) were stirred overnight at 70° C. The mixture was poured into water and extracted with dichloromethane. The organic layers were washed with NaHCO$_3$ (aq), dried over MgSO$_4$ and the solvent was removed i.vac.
Yield: 15.2 g (93%)

(360b) 2-Bromo-5-fluoro-4-nitropyridine 1-oxide

Prepared analogously to example 83b from 2-bromo-5-fluoropyridine 1-oxide, conc. sulphuric acid and conc. nitric acid
Yield: 11 g (60%)

(360c) 2-Bromo-5-(methylamino)-4-nitropyridine 1-oxide

2-Bromo-5-fluoro-4-nitropyridine 1-oxide (11.2 g, 47 mmol) and 2 N methylamine (solution in THF) (48 mL, 96 mmol) in 150 mL THF was stirred for 5 min at ambient temperature. Water was poured into the mixture and THF was removed i.vac. The solid was filtered, washed with water and dried at 50° C. i. vac.
Yield: 10 g (86%)

(360d) 6-Bromo-N-methyl-4-nitropyridin-3-amine

2-Bromo-5-(methylamino)-4-nitropyridine 1-oxide (10.0 g, 40.4 mmol) in 200 mL dichloromethane was mixed with phosphorous tribromide (10 mL, 106 mmol) in 50 mL dichloromethane at 10° C. and stirred for 10 minutes at ambient temperature. Water and methanol were added and the mixture was extracted with dichloromethane. The organic layers were washed with Na$_2$CO$_3$ (aq.) dried over MgSO$_4$. The residue was triturated with ethanol, filtered and dried at 50° C. i. vac.
Yield: 7.7 g (83%)

(360e) 6-Bromo-N$^3$-methylpyridine-3,4-diamine

Prepared analogously to example 83d by hydrogenation of 6-bromo-N-methyl-4-nitropyridin-3-amine using Raney nickel in THF.
Yield: quant.
mass spectrum: (M+H)$^+$=202/204 (bromine isotopes)

(360f) 1-(4-Amino-6-bromopyridin-3-yl)-3-(2-chloro-6-fluorophenyl)-1-methyl-thiourea To the product obtained in (360e) (2.61 g, 12.9 mmol) in 20 mL THF and 10 mL methanol was added 1-chloro-3-fluoro-2-isothiocyanatobenzene (2.42 g, 12.9 mmol) and the mixture stirred at ambient temperature for 16 h. 25 mL methanol and 75 mL water were added and the mixture supersounded for 10 min. The precipitate was filtered off, washed with a mixture water/methanol=2:1 and dried at 60° C.
Yield: 4.23 g (84%)
mass spectrum: (M+H)$^+$=389/391/393 (chlorine and bromine isotopes)
R$_t$ value: 1.72 min (E7)

(360g) 6-Bromo-N-(2-chloro-6-fluorophenyl)-3-methyl-3H-imidazo[4,5-c]pyridin-2-amine To the product obtained in (360f) (4.23 g, 10.9 mmol) in 25 mL DMF was added DIC (3.5 mL, 22.4 mmol) and the mixture stirred at 100° C. for 3d. Methanol and conc. ammonia were added and the product purified by RP-HPLC(C-18 X-Bridge; eluent-gradient: water+0.15% conc. ammonia/acetonitrile=90:10→0:100). The product fractions were concentrated i. vac., the precipitate was filtered off, washed with water and dried at 60° C.
Yield: 1.36 g (35%)
mass spectrum: (M+H)$^+$=355/357/359 (chlorine and bromine isotopes)
R$_t$ value: 1.59 min (E7)

(360h) Methyl 2-(2-chloro-6-fluorophenylamino)-3-methyl-3H-imidazo[4,5-c]pyridine-6-carboxylate To 6-bromo-N-(2-chloro-6-fluorophenyl)-3-methyl-3H-imidazo[4,5-c]pyridin-2-amine (1.36 g, 3.8 mmol) in 25 mL methanol and 5 mL DMF was added 1,1'-Bis-(diphenylphosphino)-ferrocene (150 mg, 0.27 mmol) and palladium-(II)-acetate (60 mg, 0.27 mmol) at 80° C. and stirred for 14 h under carbon monoxide at 6.5 bar. The mixture was filtered and the solvent removed i. vac. The residue was purified by HPLC (C18 StableBond, 8 µm, eluent: H$_2$O+0.15% HCOOH+10-100% acetonitrile).
Yield: 1 g (80%)
mass spectrum: (M+H)+=335/337/339 (chlorine isotopes)
R$_t$ value: 1.23 min (E9)

(360i) 2-(2-Chloro-6-fluorophenylamino)-3-methyl-N-(4-trifluoromethyl-pyridin-2-yl)-3-H-imidazo[4,5-c]pyridine-6-carboxamide To 2-amino-4-trifluoromethyl-pyridine (60 mg, 0.37 mmol) in 3 mL THF was added trimethylaluminium (1N in hexane, 400 µL, 0.40 mmol) and stirred at ambient temperature for 10 min. Then methyl 2-(2-chloro-6-fluorophenylamino)-3-methyl-3H-imidazo[4,5-c]pyridine-6-carboxylate (100 mg, 0.30 mmol) was added and stirred at 40° C. for 16 h. Methanol and conc. acetic acid were added and the product purified by RP-HPLC (0-18 StableBond; eluent-gradient: water+0.15% HCOOH/acetonitrile=90:10→0:100). The product fractions were concentrated i. vac., made alkaline with ammonia, the precipitate was filtered off, washed with water and dried at 60° C.
Yield: 67 mg (48%)
mass spectrum: (M+H)$^+$=465/467/469 (chlorine isotopes);
R$_t$ value: 2.17 min (E7)

In analogy with the above described example, the following compounds were prepared:

| No. | Structural formula / Name | Yield | Mass peak(s) | $R_f$ value or $R_t$ |
|---|---|---|---|---|
| 361 | N-(4-Bromophenyl)-2-(2-chloro-6-fluoro-phenylamino)-3-methyl-3H-imidazo[4,5-c]pyridine-6-carboxamide | 6.3% | $(M + H)^+$ = 474/476/478 (chlorine isotopes) | 2.1 min (E7) |
| 364 | 2-(2,6-Dichlorophenylamino)-3-methyl-N-(4-trifluoromethyl-pyridin-2-yl)-3H-imidazo[4,5-c]pyridine-6-carboxamide | 2.4% | $(M + H)^+$ = 481/483/485 (chlorine isotopes) | 2.26 min. (E7) |
| 365 | N-(4-Bromophenyl)-2-(2,6-dichlorophenylamino)-3-methyl-3H-imidazo[4,5-c]pyridine-6-carboxamide | 4.5% | $(M + H)^+$ = 490/492/494 (chlorine isotopes) | 2.19 min (E7) |
| 389 | 2-(2-Chloro-6-fluorophenylamino)-N-(4,4-dimethylcyclohexyl)-3-methyl-3H-imidazo[4,5-c]-pyridine-6-carboxamide | 6.9% | $(M + H)^+$ = 429/431/433 (chlorine isotopes) | 2.05 min (E7) |
| 406 | 2-(2,6-Dichlorophenylamino)-N-(4,4-dimethylcyclohexyl)-3-methyl-3H-imidazo[4,5-c]pyridine-6-carboxamide | 3.9% | $(M + H)^+$ = 446/448/450 (chlorine isotopes) | 2.13 min (E7) |
| 417 | 2-(2-Chloro-6-fluoro-phenylamino)-3-methyl-N-(spiro[2.5]octan-6-yl)-3H-imidazo[4,5-c]pyridine-6-carboxamide | 4.1% | $(M + H)^+$ = 428/430/432 (chlorine isotopes) | 2.13 min (E7) |

| No. | Structural formula Name | Yield | Mass peak(s) | $R_f$-value or $R_t$ |
|---|---|---|---|---|
| 424 | 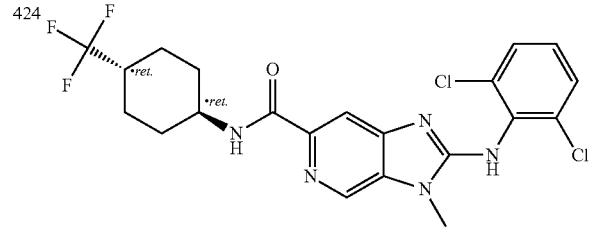<br>2-(2,6-Dichlorophenylamino)-3-methyl-N-((1r,4r)-4-trifluoromethyl-cyclohexyl)-3H-imidazo[4,5-c]pyridine-6-carboxamide | 2.7% | $(M + H)^+$ = 486/488/490 (chlorine isotopes) | 2.00 min (E7) |
| 425 | 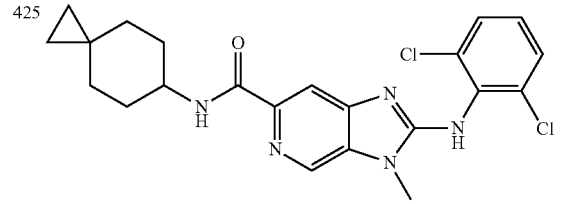<br>2-(2,6-Dichlorophenylamino)-3-methyl-N-(spiro[2.5]octan-6-yl)-3H-imidazo[4,5-c]-pyridine-6-carboxamide | 3.5% | $(M + H)^+$ = 444/446/448 (chlorine isotopes) | 2.05 min (E7) |
| 431 | 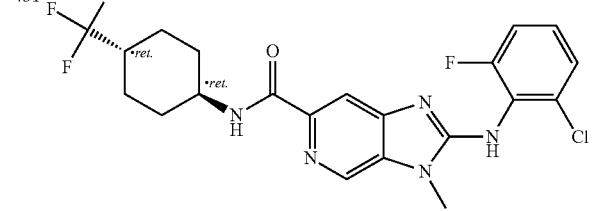<br>2-(2-Chloro-6-fluorophenylamino)-3-methyl-N-((1r,4r)-4-trifluoromethyl-cyclohexyl)-3H-imidazo[4,5-c]pyridine-6-carboxamide | 3.5% | $(M + H)^+$ = 470/472/474 (chlorine isotopes) | 1.92 min (E7) |
| 444 | 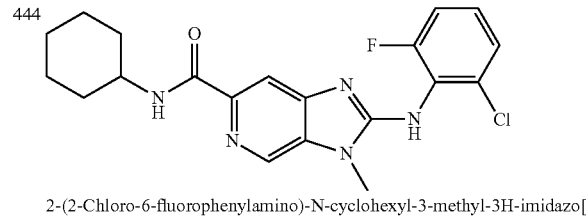<br>2-(2-Chloro-6-fluorophenylamino)-N-cyclohexyl-3-methyl-3H-imidazo[4,5-c]-pyridine-6-carboxamide | 5.1% | $(M + H)^+$ = 401/403/405 (chlorine isotopes) | 1.76 min (E7) |
| 445 | 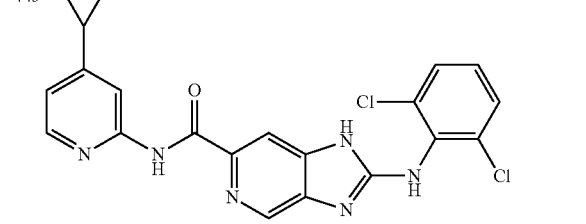<br>N-(4-Cyclopropylpyridin-2-yl)-2-(2,6-dichlorophenylamino)-1H-imidazo[4,5-c]-pyridine-6-carboxamide | 2.2% | $(M + H)^+$ = 439/441/443 (chlorine isotopes) | 1.56 min (E9) |
| 451 | 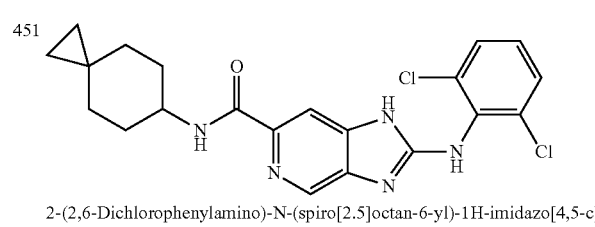<br>2-(2,6-Dichlorophenylamino)-N-(spiro[2.5]octan-6-yl)-1H-imidazo[4,5-c]pyridine-6-carboxamide | 3.5% | $(M + H)^+$ = 430/432/434 (chlorine isotopes) | 1.24 min (F8) |

-continued

| Structural formula No. Name | Yield | Mass peak(s) | R$_f$ value or R$_t$ |
|---|---|---|---|
| 462 N-(4-Cyclopropylpyridin-2-yl)-2-(2,6-dichlorophenylamino)-3-methyl-3H-imidazo[4,5-c]pyridine-6-carboxamide | Σ: 3.7% | (M + H)+ = 453/455/457 (chlorine isotopes) | 1.68 min (E9) |
| 472 N-(4-Bromophenyl)-2-(3,5-dichloropyridin-4-ylamino)-3-methyl-3H-imidazo[4,5-c]-pyridine-6-carboxamide | Σ: 1.8% | (M + H)+ = 492/494/496 (chlorine isotopes) | 2.27 min (E7) |
| 478 2-(3,5-Dichloropyridin-4-ylamino)-N-(4,4-dimethylcyclohexyl)-3-methyl-3H-imidazo[4,5-c]pyridine-6-carboxamide | Σ: 4.6% | (M + H )+ = 447/449/451 (chlorine isotopes) | 2.29 min (B7) |
| 482 2-(3,5-Dichloropyridin-4-ylamino)-3-methy-N-(4-trifluoromethyl-pyridin-2-yl)-3H-imidazo[4,5-c]pyridine-6-carboxamide | Σ: 0.2% | (M + H)+ = 482/484/486 (chlorine isotopes) | 2.29 min (B7) |
| 487 N-Cyclohexyl-2-(2,6-dichlorophenylamino)-3-methyl-3H-imidazo[4,5-c]pyridine-6-carboxamide | Σ: 8.6% | (M + H)+ = 418/420/422 (chlorine isotopes) | 1.87 min (B7) |

-continued

| No. | Structural formula Name | Yield | Mass peak(s) | $R_f$-value or $R_t$ |
|---|---|---|---|---|
| 504 | 2-(2-Chloro-6-fluorophenylamino)-3-methyl-N-((3-trifluoromethyl-pyridin-2-yl)-methyl)-3H-imidazo[4,5-c]pyridine-6-carboxamide | Σ: 9.0% | (M + H)+ = 478/480/482 (chlorine isotopes) | 1.77 min (E7) |
| 515 | 2-(3,5-Dichloropyridin-4-ylamino)-3-methyl-N-((1r,4r)-4-trifluoromethyl-cyclohexyl)-3H-imidazo[4,5-c]pyridine-6-carboxamide | Σ: 11.9% | (M + H)+ = 487/489/491 (chlorine isotopes) | 2.12 min (E7) |
| 522 | 2-(2-Chloro-6-fluorophenylamino)-N-((3-cyclopropylpyridin-2-yl)-methyl)-3-methyl-3H-imidazo[4,5-c]pyridine-6-carboxamide | Σ: 7.8% | (M + H)+ = 450/452/454 (chlorine isotopes) | 1.5 min (E7) |
| 528 | 2-(2,6-Dichlorophenylamino)-3-methyl-N-((3-trifluoromethyl-pyridin-2-yl)-methyl)-3H-imidazo[4,5-c]pyridine-6-carboxamide | Σ: 8.5% | (M + H)+ = 495/497/499 (chlorine isotopes) | 1.28 min (F8) |
| 550 | 2-(3,5-Dichloropyridin-4-ylamino)-3-methyl-N-((3-trifluoromethyl-pyridin-2-yl)-methyl)-3H-imidazo[4,5-c]pyridine-6-carboxamide | Σ: 9.0% | (M + H)+ = 496/498/500 (chlorine isotopes) | 1.28 min (E7) |
| 724 | 2-(2,6-Dichlorophenylamino)-3-methyl-N-(4,5-dimethyl-pyridin-2-yl)-3H-imidazo[4,5-c]pyridine-6-carboxamide | Σ: 6.2% | (M + H)+ = 441/443/445 (chlorine isotopes) | 1.59 min (E9) |

| Structural formula No. Name | Yield | Mass peak(s) | $R_f$-value or $R_t$ |
|---|---|---|---|
| 726 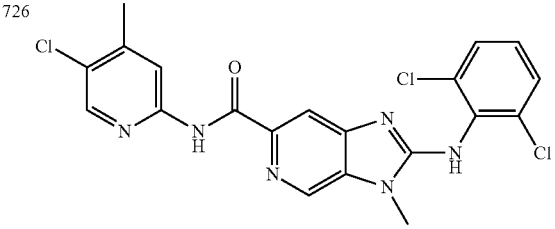 2-(2,6-Dichlorophenylamino)-3-methyl-N-(5-chloro-4-methyl-pyridin-2-yl)-3H-imidazo[4,5-c]pyridine-6-carboxamide | Σ: 3.1% | (M + H)+ = 461/463/465/467 (chlorine isotopes) | 2.20 min (E9) |
| 734 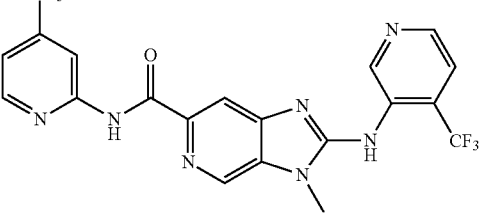 2-(4-Trifluoromethyl-pyridin-3-ylamino)-3-methyl-N-(4-trifluoromethyl-pyridin-2-yl)-3H-imidazo[4,5-c]pyridine-6-carboxamide | Σ: 3.3% | (M + H)+ = 482/484/486 (chlorine isotopes) | 2.07 min (E9) |

Example 366

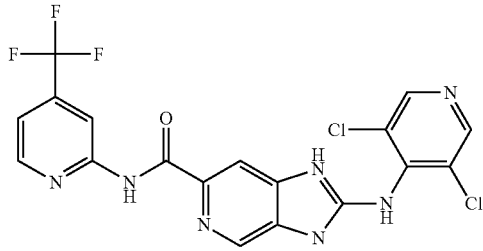

2-(3,5-Dichloropyridin-4-ylamino)-N-(4-trifluoromethyl-pyridin-2-yl)-1H-imidazo[4,5-c]pyridine-6-carboxamide (366a) Methyl-4-aminopicolinate A mixture of 4-aminopicolinic acid (2.50 g, 18.1 mmol) and conc. sulfuric acid (2 mL, 37.3 mmol) in 50 mL methanol was refluxed for 20 h. The mixture was concentrated i. vac., then 50 mL dichloromethane were added and made basic by addition of conc. ammonia (aq). Then water and NaCl (aq, sat.) were added and the aqueous layer was extracted with methylenechloride/methanol=9:1. The combined organic layers were dried over $MgSO_4$ and then evaporated to dryness.

Yield: 2.05 g (74%)
mass spectrum: $(M+H)^+=153$ (366b) Methyl-4-amino-5-nitropicolinate Prepared analogously to example 83b from methyl-4-aminopicolinate, conc. sulphuric acid and potassium nitrate.

Yield: 55%; mass spectrum: $(M+H)^+=198$; $R_t$ value: 1.05 min (E7)

(366c) 4-Amino-5-nitropicolinic acid

A mixture of methyl-4-amino-5-nitropicolinate (200 mg, 1.01 mmol) and NaOH (aq, 1M, 2.0 mL, 2.0 mmol) in methanol was stirred at ambient temperature for 10 min. The mixture was acidified by addition of HCl (aq, 1M, 2.1 mL, 2.1 mmol) and concentrated i. vac. and the aqueous residing mixture filtered. The solid was washed with water and dried i. vac.

Yield: 180 mg (97%)

(366d) 4-Amino-5-nitro-N-(4-trifluoromethyl-pyridin-2-yl)-picolinamide

A mixture of 4-amino-5-nitropicolinic acid (180 mg, 1.0 mmol) in 10 mL dichloromethane with 280 μL thionyl chloride was refluxed for 1 h, cooled to ambient temperature and concentrated to dryness i. vac. The residue was mixed with 10 mL THF and 10 mL dichloromethane and pyridine (100 μL, 1.3 mmol), and 4-trifluoromethyl-pyridin-2-amine (160 mg, 1.0 mmol) was added to the mixture. After stirring for 45 min the mixture was disturbed with methanol and concentrated i.vac. The residue was purified by chromatography on HPLC (C18 StableBond, eluent: $H_2O+0.15\%$ HCOOH+10-100% acetonitrile)

Yield: 160 mg (50%)
mass spectrum: $(M+H)^+=328$
$R_t$ value: 2.15 min (E7)

(366e) 4,5-Diamino-N-(4-trifluoromethyl-pyridin-2-yl)-picolinamide

Prepared analogously to example 83d by hydrogenation of 4-amino-5-nitro-N-(4-trifluoromethyl-pyridin-2-yl)-picolinamide using palladium/charcoal 10% in methanol and THF.

Yield: 96%
mass spectrum: (M+H)⁺=298
R$_t$ value: 1.42 min (E7)

(366f) 5-Amino-4-(3-(3,5-dichloropyridin-4-yl)-N-(4-trifluoromethyl-pyridin-2-yl)-picolinamide Prepared analogously to example 360f from 4,5-diamino-N-(4-trifluoromethyl-pyridin-2-yl)-picolinamide and 3,5-dichloro-4-isothiocyanatopyridine in THF and acetonitrile.
Yield: 76%
mass spectrum: (M+H)⁺=502
R$_t$ value: 1.97 min (E7)

(366e) 2-(3,5-Dichloropyridin-4-ylamino)-N-(4-trifluoromethyl-pyridin-2-yl)-1H-imidazo[4,5-c]pyridine-6-carboxamide Prepared analogously to example 360g from 5-amino-4-(3-(3,5-dichloropyridin-4-yl)-N-(4-trifluoromethyl-pyridin-2-yl)-picolinamide and DIC in acetonitrile
Yield: 89%
mass spectrum: (M+H)⁺=468/470/472 (chlorine isotopes)
R$_t$ value: 2.02 min (E7)

In analogy with the above described example, the following compounds were prepared:

| No. | Structural formula Name | Yield | Mass peak(s) | R$_f$ value or R$_t$ |
|---|---|---|---|---|
| 727 | 2-(2-Fluoro-6-trifluoromethyl-phenylamino)-N-(4-trifluoromethyl-pyridin-2-yl)-1H-imidazo[4,5-c]pyridine-6-carboxamide | Σ: 13.6% | (M + H)+ = 485 | 2.18 min (E7) |
| 728 | 2-(2-Chloro-6-trifluoromethyl-phenylamino)-N-(4-trifluoromethyl-pyridin-2-yl)-1H-imidazo[4,5-c]pyridine-6-carboxamide | Σ: 10.1% | (M + H)+ = 501/503 (chlorine isotopes) | 2.21 min (E7) |
| 729 | 2-(2-Chloro-6-fluoro-phenylamino)-N-(4-trifluoromethyl-pyridin-2-yl)-1H-imidazo[4,5-c]pyridine-6-carboxamide | Σ: 10.7% | (M + H)+ = 451/453 (chlorine isotopes) | 2.13 min (E7) |
| 730 | 2-(2,6-Dichloro-4-fluoro-phenylamino)-N-(4-trifluoromethyl-pyridin-2-yl)-1H-imidazo[4,5-c]pyridine-6-carboxamide | Σ: 2.9% | (M + H)+ = 485/487/489 (chlorine isotopes) | 1.48 min (F7) |

-continued

| No. | Structural formula Name | Yield | Mass peak(s) | $R_f$ value or $R_t$ |
|---|---|---|---|---|
| 731 | 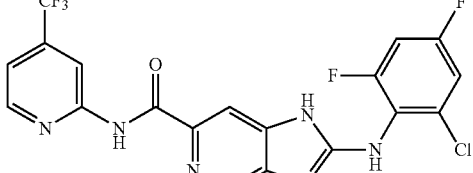<br>2-(2-Chloro-4,6-difluoro-phenylamino)-N-(4-trifluoromethyl-pyridin-2-yl)-1H-imidazo[4,5-c]pyridine-6-carboxamide | Σ: 4.0% | (M + H)+ = 469/471 (chlorine isotopes) | 1.48 min (F7) |
| 732 | 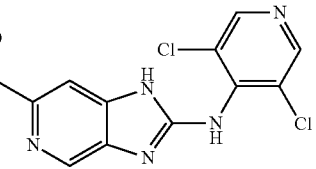<br>2-(3,5-Dichloro-pyridin-4-yl-amino)-N-(4-bromo-phenyl)-1H-imidazo[4,5-c]pyridine-6-carboxamide | Σ: 0.5% | (M +H)+ = 477/479/481/483 (bromine and chlorine isotopes) | 1.39 min (F8) |
| 733 | 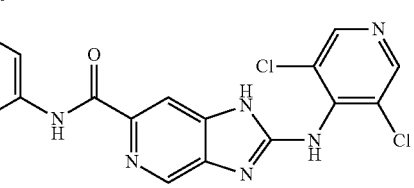<br>2-(3,5-Dichloro-pyridin-4-yl-amino)-N-(6-methyl-4-trifluoromethyl-pyridin-2-yl)-1H-imidazo[4,5-c]pyridine-6-carboxamide | Σ: 7.0% | (M + H)+ = 482/484/486 (chlorine isotopes) | 1.46 min (F8) |
| 736 | 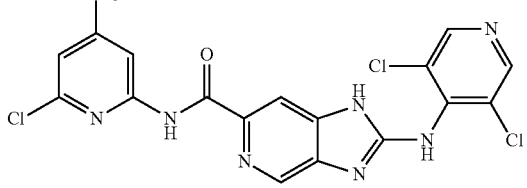<br>2-(3,5-Dichloro-pyridin-4-yl-amino)-N-(6-chloro-4-trifluoromethyl-pyridin-2-yl)-1H-imidazo[4,5-c]pyridine-6-carboxamide | Σ: 6.8% | (M + H)+ = 502/504/506/508 (chlorine isotopes) | 2.20 min (E9) |

Example 396

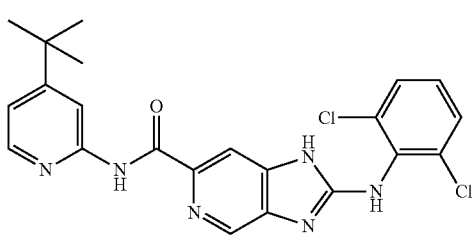 [SMILES: CC(C)(C)c1ccnc(NC(=O)c2cc3[nH]c(Nc4c(Cl)cccc4Cl)nc3cn2)c1]

N-(4-tert.-Butyl-pyridin-2-yl)-2-(2,6-dichlorophenylamino)-1H-imidazo[4,5-c]pyridine-6-carboxamide

(396a) Methyl-4-aminopicolinate

Prepared analogously to example 366a from 4-aminopicolinic acid and sulfuric acid in methanol.
Yield: 74%
mass spectrum: (M+H)$^+$=153

(396b) Methyl-4-amino-5-nitro-picolinate

Prepared analogously to example 83b from methyl-4-aminopicolinate, conc. sulphuric acid and potassium nitrate.
Yield: 55%
mass spectrum: (M+H)$^+$=198
$R_t$ value: 1.05 min (E7)

(396c) Methyl 4,5-diamino-picolinate

Prepared analogously to example 83d by hydrogenation of methyl-4-amino-5-nitropicolinate using palladium/charcoal 10% in THF.
Yield: 98%

(396d) Methyl 5-amino-4-(3-(2,6-dichlorophenyl) thioureido)picolinate

Prepared analogously to example 360f from methyl 4,5-diamino-picolinate and 1,3-dichloro-2-isothiocyanato-benzene in THF and methanol.
Yield: 90%

(396e) Methyl 2-(2,6-dichlorophenylamino)-1H-imidazo[4,5-c]pyridine-6-carboxylate Prepared analogously to example 360g from methyl 5-amino-4-(3-(2,6-dichlorophenyl)-thioureido)-picolinate and DIC in acetonitrile
Yield: 94%
mass spectrum: (M+H)+=337/39/41 (chlorine isotopes)

(396f) N-(4-tert.-Butylpyridin-2-yl)-2-(2,6-dichlorophenylamino)-1H-imidazo[4,5-c]pyridine-6-carboxamide Prepared analogously to example 360i from methyl 2-(2,6-dichlorophenylamino)-1H-imidazo[4,5-c]pyridine-6-carboxylate, 2 M trimethyl aluminium (solution in hexane) and 4-tert.-butylpyridin-2-amine in THF.

Yield: 37% mass spectrum: (M+H)$^+$=455/57/59 (chlorine isotopes)

$R_t$ value: 1.8 min (E9)

In analogy with the above described example, the following compounds were prepared:

| Structural formula No. Name | Yield | Mass peak(s) | $R_f$ value or $R_t$ |
|---|---|---|---|
| 414  2-(2,6-Dichlorophenylamino)-N-(4-trifluoromethyl-pyridin-2-yl)-1H-imidazo[4,5-c]pyridine-6-carboxamide | Σ: 12.3% | (M + H)+ = 467/469/471 (chlorine isotopes) | 1.43 min (F8) |
| 427  N-(4-Chloro-5-methyl-pyridin-2-yl)-2-(2,6-dichlorophenylamino)-1H-imidazo[4,5-c]pyridine-6-carboxamide | Σ: 3.7% | (M + H)+ = 447/449/451 (chlorine isotopes) | 2.80 min (C2) |
| 440  N-(4-(Cyclopentyloxy)pyridin-2-yl)-2-(2,6-dichlorophenylamino)-1H-imidazo[4,5-c]pyridine-6-carboxamide | Σ: 2% | (M + H)+ = 483/485/487 (chlorine isotopes) | 1.23 min (E8) |
| 477  2-(2,6-Dichlorophenylamino)-N-(2-trifluoromethyl-benzyl)-1H-imidazo[4,5-c]pyridine-6-carboxamide | Σ: 5% | (M + H)+ = 480/482/484 (chlorine isotopes) | 1.29 min (F8) |

| Structural formula No. Name | Yield | Mass peak(s) | $R_f$ value or $R_t$ |
|---|---|---|---|
| 481 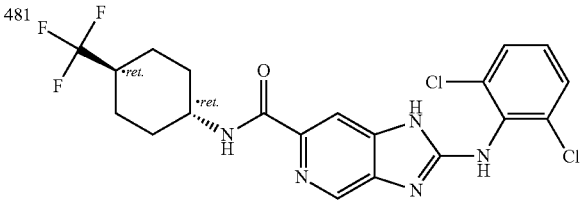<br>2-(2,6-Dichlorophenylamino)-N-((1r,4r)-4-trifluoromethyl-cyclohexyl)-1H-imidazo[4,5-c]pyridine-6-carboxamide | Σ: 1.8% | (M + H)+ = 472/474/476 (chlorine isotopes) | 1.23 min (F8) |
| 495 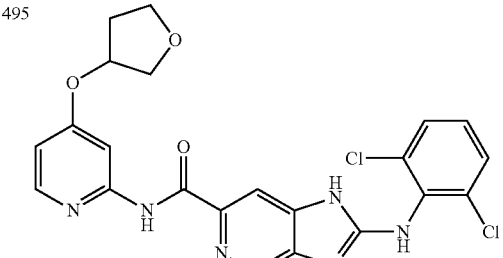<br>2-(2,6-Dichlorophenylamino)-N-(4-(tetrahydrofuran-3-yl-oxy)-pyridin-2-yl)-1H-imidazo[4,5-c]pyridine-6-carboxamide | Σ: 1.4% | (M + H)+ = 485/487/489 (chlorine isotopes) | 1.11 min (F8) |
| 509 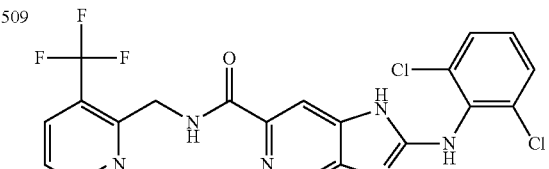<br>2-(2,6-Dichlorophenylamino)-N-((3-trifluoromethyl-pyridin-2-yl)methyl)-1H-imidazo[4,5-c]pyridine-6-carboxamide | Σ: 3.6% | (M + H)+ = 481/483/485 (chlorine isotopes) | 1.2 min (F8) |
| 716 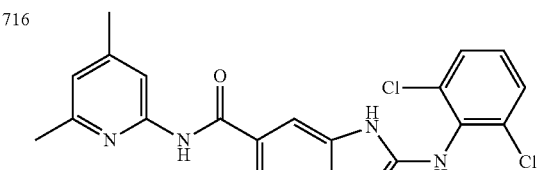<br>2-(2,6-Dichlorophenylamino)-N-(4,6-dimethyl-pyridin-2-yl)-1H-imidazo[4,5-c]pyridine-6-carboxamide | Σ: 10.8% | (M + H)+ = 427/429/431 (chlorine isotopes) | 1.51 min (E9) |
| 717 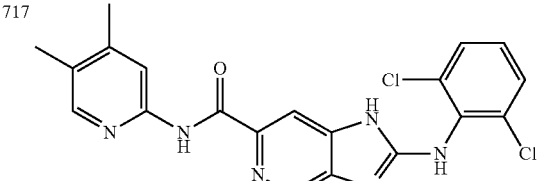<br>2-(2,6-Dichlorophenylamino)-N-(4,5-dimethyl-pyridin-2-yl)-1H-imidazo[4,5-c]pyridine-6-carboxamide | Σ: 12.1% | (M + H)+ = 427/429/431 (chlorine isotopes) | 1.47 min (E9) |
| 718 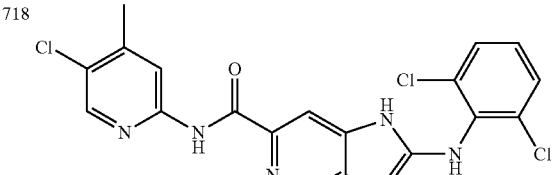<br>2-(2,6-Dichlorophenylamino)-N-(5-chloro-4-methyl-pyridin-2-yl)-1H-imidazo[4,5-c]pyridine-6-carboxamide | Σ: 8.8% | (M +H)+ = 447/449/451/453 (chlorine isotopes) | 1.99 min (E9) |

| No. | Structural formula Name | Yield | Mass peak(s) | $R_f$ value or $R_t$ |
|---|---|---|---|---|
| 719 | 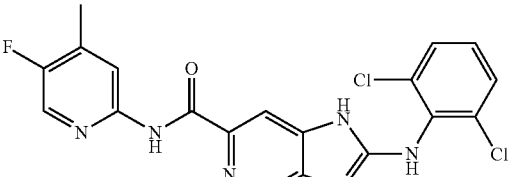<br>2-(2,6-Dichlorophenylamino)-N-(5-fluoro-4-methyl-pyridin-2-yl)-1H-imidazo[4,5-c]pyridine-6-carboxamide | Σ: 11.8% | (M + H)+ = 431/433/435 (chlorine isotopes) | 1.81 min (E9) |
| 720 | 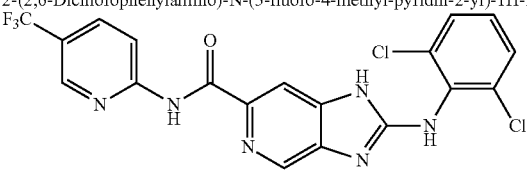<br>2-(2,6-Dichlorophenylamino)-N-(5-trifluoromethyl-pyridin-2-yl)-1H-imidazo[4,5-c]pyridine-6-carboxamide | Σ: 7.4% | (M + H)+ = 467/469/471 (chlorine isotopes) | 2.04 min (E9) |
| 721 | 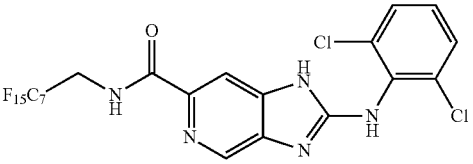<br>2-(2,6-Dichlorophenylamino)-N-(2,2,3,3,4,4,5,5,6,6,7,7,8,8,8-pentadecafluoro-octyl)-1H-imidazo[4,5-c]pyridine-6-carboxamide | Σ: 17% | (M + H)+ = 704/706/708 (chlorine isotopes) | |
| 722 | 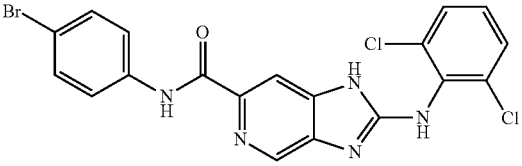 [SMILES: O=C(Nc1ccc(Br)cc1)c1cc2[nH]c(Nc3c(Cl)cccc3Cl)nc2cn1]<br>2-(2,6-Dichlorophenylamino)-N-(4-bromo-phenyl)-1H-imidazo[4,5-c]pyridine-6-carboxamide | Σ: 17% | (M + H)+ = 476/478/480/482 (bromine and chlorine isotopes) | |
| 723 | 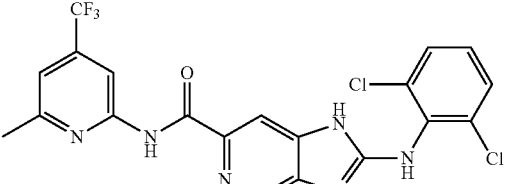<br>2-(2,6-Dichlorophenylamino)-N-(6-methyl-4-trifluoromethyl-pyridin-2-yl)-1H-imidazo[4,5-c]pyridine-6-carboxamide | Σ: 5.4% | (M + H)+ = 481/483/485 (chlorine isotopes) | 2.13 min (E9) |
| 725 | 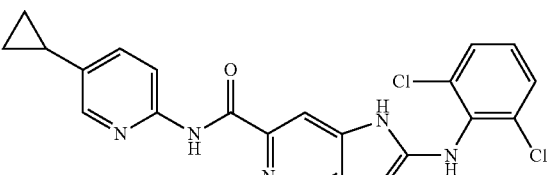<br>2-(2,6-Dichlorophenylamino)-N-(5-cyclopropyl-pyridin-2-yl)-1H-imidazo[4,5-c]pyridine-6-carboxamide | Σ: 6.7% | (M + H)+ = 439/441/443 (chlorine isotopes) | 1.74 min (E9) |
| 735 | 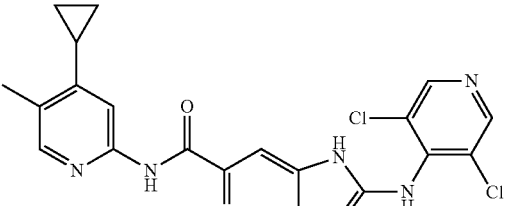<br>2-(3,5-Dichloro-pyridin-4-yl-amino)-N-(4-cyclopropyl-5-methyl-pyridin-2-yl)-1H-imidazo[4,5-c]pyridine-6-carboxamide | Σ: 11.6% | (M + H)+ = 454/456/458 (chlorine isotopes) | 1.53 min (E9) |

| Structural formula No. Name | | Yield | Mass peak(s) | $R_f$-value or $R_t$ |
|---|---|---|---|---|
| 737 | 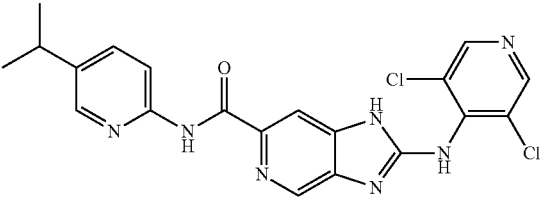 [SMILES: CC(C)c1ccc(NC(=O)c2cc3[nH]c(Nc4c(Cl)cncc4Cl)nc3cn2)nc1] 2-(3,5-Dichloro-pyridin-4-yl-amino)-N-(5-isopropyl-pyridin-2-yl)-1H-imidazo[4,5-c]pyridine-6-carboxamide | Σ: 6.5% | (M + H)+ = 442/444/446 (chlorine isotopes) | 1.27 min (F9) |
| 738 | 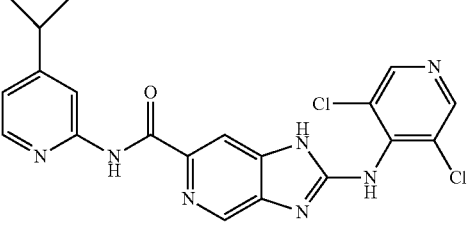 2-(3,5-Dichloro-pyridin-4-yl-amino)-N-(4-cyclobutyl-pyridin-2-yl)-1H-imidazo[4,5-c]pyridine-6-carboxamide | Σ: 8.8% | (M + H)+ = 454/456/458 (chlorine isotopes) | 1.69 min (E9) |
| 739 | 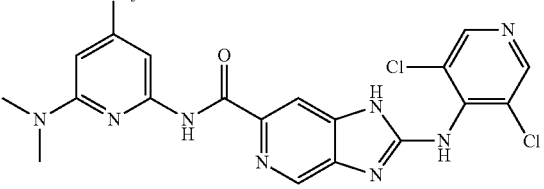 2-(3,5-Dichloro-pyridin-4-yl-amino)-N-(6-dimethylamino-4-trifluoromethyl-pyridin-2-yl)-1H-imidazo[4,5-c]pyridine-6-carboxamide | Σ: 3.4% | (M + H)+ = 511/513/515 (chlorine isotopes) | 2.93 min (C5) |
| 740 | 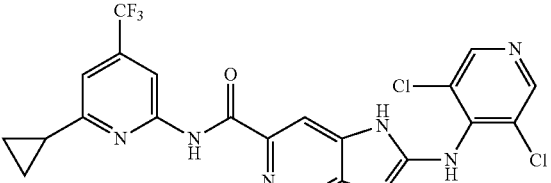 2-(3,5-Dichloro-pyridin-4-yl-amino)-N-(6-cyclopropyl-4-trifluoromethyl-pyridin-2-yl)-1H-imidazo[4,5-c]pyridine-6-carboxamide | Σ: 3.4% | (M + H)+ = 508/510/512 (chlorine isotopes) | 1.55 min (F8) |

Biological Data

Title compounds of the examples were tested in the biological test described above and were found to exhibit 50% inhibition of mPGES-1 at a concentration of 10 μM or below. For example, the following representative compounds of the examples exhibited the following percentage inhibitions at 10 μM (unless otherwise specified):

| example | % inhib. |
|---|---|
| 83 | 100 |
| 137 | 100 |
| 360 | 100 |
| 361 | 100 |
| 364 | 100 |
| 365 | 100 |
| 366 | 100 |
| 389 | 100 |
| 396 | 100 |
| 406 | 100 |
| 414 | 100 |
| 417 | 100 |
| 424 | 100 |
| 425 | 100 |
| 427 | 98 |
| 431 | 100 |
| 440 | 100 |
| 444 | 100 |
| 445 | 98 |
| 451 | 99 |
| 462 | 94 |
| 463 | 97 |
| 472 | 96 |
| 477 | 97 |
| 478 | 100 |
| 481 | 98 |
| 482 | 98 |

-continued

| example | % inhib. |
|---|---|
| 487 | 100 |
| 495 | 86 |
| 504 | 100 |
| 509 | 97 |
| 440 | 100 |
| 515 | 100 |
| 522 | 100 |
| 528 | 96 |
| 550 | 95 |
| 716 | 100 |
| 717 | 100 |
| 718 | 100 |
| 719 | 100 |
| 720 | 100 |
| 721 | 100 |
| 722 | 100 |
| 723 | 100 |
| 724 | 100 |
| 725 | 100 |
| 515 | 100 |
| 522 | 100 |
| 726 | 100 |
| 727 | 99 |
| 728 | 98 |
| 729 | 100 |
| 730 | 100 |
| 731 | 100 |
| 732 | 100 |
| 733 | 99 |
| 734 | 99 |
| 735 | 99 |
| 736 | 98 |
| 737 | 97 |
| 738 | 100 |
| 739 | 100 |
| 740 | 100 |
| 731 | 100 |

The invention claimed is:
1. A compound of formula I,

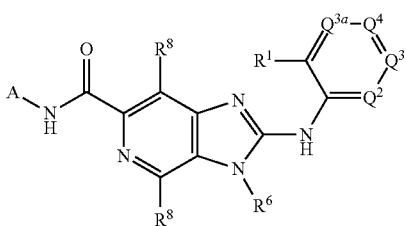

in which $Q^2$, $Q^3$, $Q^{3a}$ and $Q^4$ respectively represent —C($R^2$)=, —C($R^3$)=, —C($R^{3a}$)= and —C($R^4$)=;
or
any one or two of $Q^2$, $Q^3$, $Q^{3a}$ and $Q^4$ may alternatively and independently represent —N=;
$R^1$ represents halo, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$, —C(O)$R^{y15}$;
$C_{1-7}$ alkyl, $C_{2-7}$ alkenyl, $C_{2-7}$ alkynyl, cycloalkyl (which latter four groups are optionally substituted by one or more substituents selected from fluoro, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$ and —C(O)$R^{y15}$); or heterocycloalkyl or heteroaryl (which latter two groups are optionally substituted by one or more substituents selected from $R^9$);
$R^2$, $R^3$, $R^{3a}$ and $R^4$:
independently represent hydrogen, halo, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$, —C(O)$R^{y15}$;
$C_{1-7}$ alkyl, $C_{2-7}$ alkenyl, $C_{2-7}$ alkynyl, cycloalkyl [which latter four groups are optionally substituted by one or more substituents selected from fluoro, —CN —N($R^{y1}$)$R^{y2}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$ and —C(O)$R^{y15}$] provided that if $R^3$ or $R^{3a}$ is a substituted $C_1$ alkyl group, then the substituent cannot be —N($R^{y5}$)—S(O)$_2$—$R^{y6}$;
or any adjacent pair of $R^1$, $R^2$, $R^3$, $R^{3a}$ and $R^4$ (i.e. $R^1$ and $R^{3a}$, $R^2$ and $R^3$, $R^3$ and $R^4$ and $R^4$ and $R^{3a}$) may be linked together to form, along with the essential carbon atoms of the $Q^2$ to $Q^4$-containing ring to which they are necessarily attached, a further 5- to 7-membered ring, optionally containing one to three heteroatoms, which ring may contain one or two further unsaturations and which is optionally substituted by one or more $C_{1-3}$ alkyl and/or =O substituents;
$R^6$ represents hydrogen;
heterocycloalkyl, aryl, heteroaryl (which latter three groups are optionally substituted by one or more substituents selected from $R^9$); or
$C_{1-6}$ alkyl, $C_{2-6}$ alkenyl, $C_{2-6}$ alkynyl, cycloalkyl, which latter four groups are optionally substituted by one or more substituents selected from fluoro, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$N($R^{y13}$)$R^{y14}$, —C(O)$R^{y15}$, heterocycloalkyl, cycloalkyl, aryl and heteroaryl (which latter four groups are optionally substituted by one or more substituents selected from $R^9$);
each $R^8$ independently represents hydrogen, halo, —N($R^{y1}$)$R^{y2}$, —O$R^{y10}$, —S(O)$_2$—$R^{y11}$; $C_{1-6}$ alkyl, $C_{2-6}$ alkenyl, $C_{2-6}$ alkynyl, cycloalkyl, —O—$C_{1-6}$ alkyl, —O—$C_{2-6}$ alkenyl, —O—$C_{2-6}$ alkynyl, —O-cycloalkyl, —O-heterocycloalkyl [which latter nine groups are optionally substituted by one or more substituents selected from fluoro, —CN, —N($R^{y1}$)$R^{y2}$, —N($R^{y3}$)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$, —C(O)$R^{y15}$, cycloalkyl, heterocycloalkyl, aryl and heteroaryl (which latter four groups are optionally substituted by one or more substituents selected from $R^9$)];
heterocycloalkyl or heteroaryl (which latter two groups are optionally substituted by one or more substituents selected from $R^9$);
A represents aryl, heteroaryl, heterocycloalkyl, cycloalkyl, $C_{1-12}$ alkyl, $C_{2-12}$ alkenyl or $C_{2-12}$ alkynyl, all of which are optionally substituted by one or more substituents selected from $R^9$;
$R^9$ represents, on each occasion when used herein:
halo, —CN, —N($R^{y1}$)$R^{y2}$, —N(V)—C(O)—$R^{y4}$, —N($R^{y5}$)—S(O)$_2$—$R^{y6}$, —C(O)O$R^{y7}$, —C(O)N($R^{y8}$)$R^{y9}$, —O$R^{y10}$, —S(O)$_m$—$R^{y11}$, —S(O)$_2$O—$R^{y12}$, —S(O)$_2$N($R^{y13}$)$R^{y14}$ and —C(O)$R^{y15}$;

$C_{1-7}$ alkyl, $C_{2-7}$ alkenyl, $C_{2-7}$ alkynyl, cycloalkyl, heterocycloalkyl [which latter five groups are optionally substituted by one or more substituents selected from fluoro, —CN, —N(R$^{y1}$)R$^{y2}$, —N(R$^{y3}$)—C(O)—R$^\circ$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and —C(O)R$^{y15}$]; or aryl or heteroaryl [which latter two groups are optionally substituted by one or more substituents selected from halo, —CN, $C_{1-7}$ alkyl, $C_{2-7}$ alkenyl, $C_{2-7}$ alkynyl, cycloalkyl (which latter four groups are optionally substituted by one or more substituents selected from fluoro and —OR$^{x2}$), —O—$C_{1-7}$ alkyl, —O—$C_{2-7}$ alkenyl, —O—$C_2$—, alkynyl and —O-cycloalkyl (which latter four groups are optionally substituted by one or more fluoro atoms)]; or any two R$^9$ substituents:
when attached to the adjacent atoms of the A group; and, in the case where the R$^9$ substituents are attached to a non-aromatic A group,
when attached to the same atoms,
may be linked together to form, together with the essential atoms of the A group to which the relevant R$^9$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or =O substituents;

m represents 0, 1 or 2;

each R$^{y4}$, R$^{y6}$, R$^{y11}$ and R$^{y15}$:
independently represent $C_{1-7}$ alkyl, $C_{2-7}$ alkenyl, $C_{2-7}$ alkynyl, cycloalkyl, which latter four groups are optionally substituted by one or more fluoro atoms;

each R$^{x2}$, R$^{y1}$, R$^{y2}$, R$^{y3}$, R$^{y5}$, R$^{y7}$, R$^{y8}$, R$^{y9}$, R$^{y10}$, R$^{y12}$, R$^{y13}$ and R$^{y14}$:
independently represent hydrogen or $C_{1-7}$ alkyl, $C_{2-7}$ alkenyl, $C_{2-7}$ alkynyl, cycloalkyl, heterocycloalkyl, which latter five groups are optionally substituted one or more substituents selected from fluoro and —OC$_{1-3}$ alkyl; or any two groups, when attached to the same nitrogen atom (i.e. R$^{y1}$ and R$^{y2}$, R$^{y8}$ and R$^{y9}$, and R$^{y13}$ and R$^{y14}$), may, together with that nitrogen atom to which they are necessarily attached, be linked together to form a 3- to 8-membered ring, optionally containing one or two further heteroatoms and which ring optionally contains one or two unsaturations and is optionally substituted by one or more $C_{1-3}$ alkyl and/or =O substituents, or a pharmaceutically acceptable salt thereof.

2. A compound according to claim 1, wherein
Q$^2$ represents —C(R$^2$)=; and
any two of Q$^3$, Q$^{3a}$ and Q$^4$ respectively represent —C(R$^3$)=, —C(R$^{3a}$)= and —C(R$^4$)=; and
the remaining one of Q$^3$, Q$^{3a}$ and Q$^4$ represents —N=;
or a pharmaceutically acceptable salt thereof.

3. A compound according to claim 1, wherein
Q$^2$, Q$^3$ and Q$^{3a}$ respectively represent —C(R$^2$)=, —C(R$^3$)= and —C(R$^{3a}$)=; and
Q$^4$ represents —N=;
or a pharmaceutically acceptable salt thereof.

4. A compound according to claim 1, wherein
Q$^2$, Q$^{3a}$ and Q$^4$ respectively represent —C(R$^2$)=, —C(R$^{3a}$)= and —C(R$^4$)=; and
Q$^3$ represents —N=;

or wherein
Q$^2$, Q$^3$ and Q$^4$ respectively represent —C(R$^2$)=, —C(R$^3$)= and —C(R$^4$)=; and
Q$^{3a}$ represents —N=;
or a pharmaceutically acceptable salt thereof.

5. A compound according to claim 1, wherein
R$^1$ represents $C_{1-4}$ alkyl (optionally substituted by one or more fluoro atoms), $C_{3-6}$ cycloalkyl or halo;
or a pharmaceutically acceptable salt thereof.

6. A compounds according to claim 1, wherein
R$^2$ represents hydrogen, $C_{1-4}$ alkyl [optionally substituted by one or more atoms selected from fluoro, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and —C(O)R$^{y15}$],
$C_{3-6}$ cycloalkyl, halo or —O—$C_{1-3}$ alkyl (optionally substituted by one or more fluoro atoms);
or a pharmaceutically acceptable salt thereof.

7. A compound according to claim 1, wherein:
R$^3$, R$^{3a}$ and R$^4$ independently represent hydrogen, $C_{1-3}$ alkyl (optionally substituted by one or more fluoro atoms) or halo;
or a pharmaceutically acceptable salt thereof.

8. A compound according to claim 1, wherein
R$^9$ represents halo, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and/or —C(O)R$^{y15}$; or $C_{1-7}$ alkyl optionally substituted by one or more substituents selected from fluoro, —CN, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_m$—R$^{y11}$, —S(O)$_2$O—R$^{y12}$, —S(O)$_2$N(R$^{y13}$)R$^{y14}$ and/or —C(O)R$^{y15}$; or aryl, heteroaryl (which latter two groups are optionally substituted by one or more substituents selected from —O—$C_{1-3}$ alkyl, —CN, halo and $C_{1-2}$ alkyl optionally substituted by one or more fluoro atoms); or any two R$^9$ groups may be linked together as defined in claim 1;
or a pharmaceutically acceptable salt thereof.

9. A compound according to claim 1, wherein
R$^8$ represents hydrogen, halo, $C_{1-3}$ alkyl [optionally substituted by one or more substituents selected from fluoro, —OR$^{y10}$, N(R$^{y1}$)R$^{y2}$, —N(R$^{y3}$)—C(O)—R$^{y4}$, and —C(O)N(R$^{y8}$)R$^{y9}$] or —OR$^{y10}$;
or a pharmaceutically acceptable salt thereof.

10. A compound according to claim 1, wherein
R$^6$ represents hydrogen or $C_{1-6}$ alkyl optionally substituted by one or more substituents selected from fluoro, —N(R$^{y1}$)R$^{y2}$, —N(R$^{y3}$)—C(O)—R$^{y4}$, —N(R$^{y5}$)—S(O)$_2$—R$^{y6}$, —C(O)OR$^{y7}$, —C(O)N(R$^{y8}$)R$^{y9}$, —OR$^{y10}$, —S(O)$_2$R$^{y11}$ and a 4- to 6-membered heterocycloalkyl group (containing two or one hetero-atom(s) selected from oxygen and nitrogen);
or a pharmaceutically acceptable salt thereof.

11. A compound according to claim 1, wherein
R$^{x2}$, R$^{y1}$, R$^{y2}$, R$^{y3}$, R$^{y5}$, R$^{y7}$, R$^{y8}$, R$^{y9}$, R$^{y10}$, R$^{y12}$, R$^{y13}$ and R$^{y14}$ independently represent hydrogen or $C_{1-4}$ alkyl optionally substituted by one or more fluoro atoms or —OC$_{1-2}$ alkyl groups; or any pair of R$^{y1}$ and R$^{y2}$, R$^{y8}$ and R$^{y9}$ and/or R$^{y13}$ and R$^{y14}$ are linked together to form a 3- to 7-membered ring, optionally containing one further nitrogen or oxygen heteroatom, one or two further double bonds, and which ring is optionally substituted by one or more $C_{1-2}$ alkyl or =O substituents;
or a pharmaceutically acceptable salt thereof.

12. A compound according to claim 1, wherein
$R^{y4}$, $R^{y6}$, $R^{y11}$ and $R^{y15}$ independently represent $C_{1-4}$ alkyl;
or a pharmaceutically acceptable salt thereof.

13. A compound according to claim 1, wherein
A represents $C_{1-12}$ linear or branched alkyl, aryl, heteroaryl, 5- or 6-membered heterocycloalkyl; or $C_{3-10}$ cycloalkyl, all of which groups are optionally substituted by one or more substituents selected from $R^9$;
or a pharmaceutically acceptable salt thereof.

14. A compound according to claim 1, wherein
A represents $C_{4-12}$ linear or branched alkyl, aryl, heteroaryl, 5- or 6-membered heterocycloalkyl; or $C_{3-7}$ cycloalkyl (all of which groups are optionally substituted by one or more substituents selected from $R^9$); or
arylmethylene, heteroarylmethylene (which latter two groups are optionally substituted by one or more groups selected from $C_{1-7}$ alkyl (optionally substituted by one or more substituents selected from fluoro and —$OR^{x2}$), halo, —CN and/or —O—$C_{1-7}$ alkyl (optionally substituted by one or more fluoro atoms));
or a pharmaceutically acceptable salt thereof.

15. A compound of formula Ia, Ib, Ic or Id:

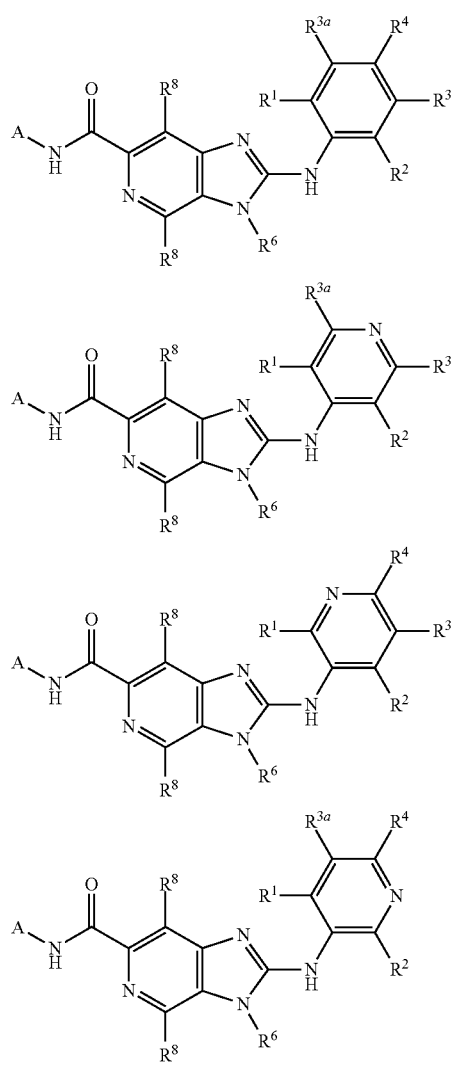

in which
$R^1$ represents $C_{1-3}$ alkyl (optionally substituted by one or more fluoro atoms), $C_{3-6}$ cycloalkyl, fluoro, chloro, bromo;

$R^2$ represents hydrogen, $C_{1-3}$ alkyl (optionally substituted by one or more fluoro atoms), $C_{3-6}$ cycloalkyl, fluoro, chloro, bromo;

$R^3$, $R^{3a}$ and $R^4$ independently represent hydrogen, fluoro, chloro, bromo, $C_{1-3}$ alkyl (optionally substituted by one or more fluoro atoms);

$R^6$ represents hydrogen or $C_{1-6}$ alkyl optionally substituted by one or more substituents selected from fluoro, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_2R^{y11}$ and a 4- to 6-membered heterocycloalkyl group (containing two or one heteroatom(s) selected from oxygen and nitrogen);

$R^8$ independently represents hydrogen, fluoro, chloro, bromo, —$OR^{y10}$ or $C_{1-3}$ alkyl (optionally substituted by one or more fluoro atoms);

A represents phenyl, pyridyl, 5- or 6-membered heterocycloalkyl, $C_{3-7}$ cycloalkyl, $C_{5-8}$ linear or branched alkyl (all of which groups are optionally substituted by one or more substituents selected from $R^9$); or benzyl, pyridylmethylene [which latter two groups are optionally substituted by one or more groups selected from $C_{1-7}$ alkyl (optionally substituted by one or more substituents selected from fluoro and —$OR^{x2}$), halo, —CN and/or —O—$C_{1-7}$ alkyl (optionally substituted by one or more fluoro atoms)];

$R^9$ represents on each occasion when used herein: halo, —CN, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and/or —$C(O)R^{y15}$, $C_{1-6}$ alkyl optionally substituted by one or more substituents selected from halo, —CN, —$N(R^{y1})R^{y2}$, —$N(R^{y3})$—$C(O)$—$R^{y4}$, —$N(R^{y5})$—$S(O)_2$—$R^{y6}$, —$C(O)OR^{y7}$, —$C(O)N(R^{y8})R^{y9}$, —$OR^{y10}$, —$S(O)_m$—$R^{y11}$, —$S(O)_2O$—$R^{y12}$, —$S(O)_2N(R^{y13})R^{y14}$ and/or —$C(O)R^{y15}$;

or any two $R^9$ substituents, when attached to the adjacent atoms of the A group and,
in the case where the $R^9$ substituents are attached to a non-aromatic A group, when attached to the same atoms, may be linked together to form, together with the essential atoms of the A group to which the relevant $R^9$ substituents are necessarily attached, a further 3- to 8-membered ring, optionally containing a further one or two heteroatoms, and which further ring optionally contains one or two unsaturations and which is optionally substituted by one or more $C_{1-3}$ alkyl and/or or =O substituents;

and the substituents $R^{x2}$, $R^{y1}$, $R^{y2}$, $R^{y3}$, $R^{y4}$, $R^{y5}$, $R^{y6}$, $R^{y7}$, $R^{y8}$, $R^{y9}$, $R^{y10}$, $R^{y11}$, $R^{y12}$, $R^{y13}$, $R^{y14}$ and $R^{y15}$ have the meaning as defined in claim 1;

or a pharmaceutically acceptable salt thereof.

16. A compound of formula Ie, If, Ig or Ih:

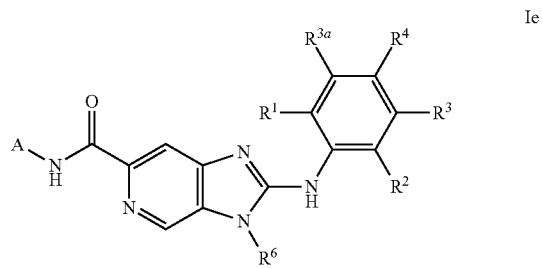

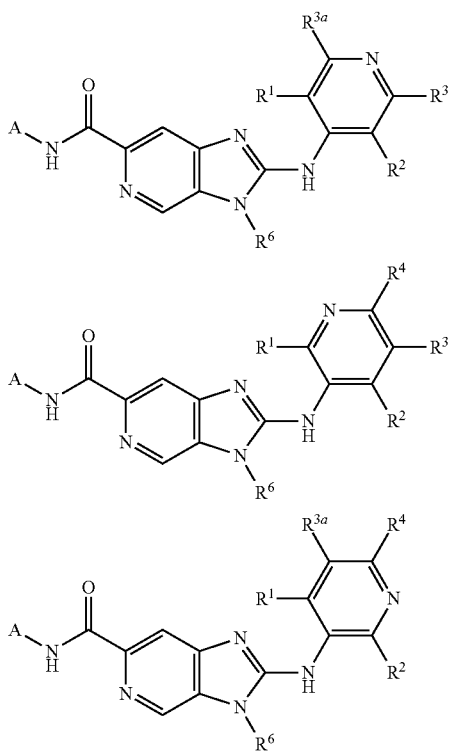

in which

R¹ represents chloro, bromo, fluoro, $C_{1-3}$ alkyl (which latter alkyl group is optionally substituted by one or more fluoro-atoms);

R² represents hydrogen, chloro, bromo, fluoro, $C_{1-3}$-alkyl (which latter alkyl group is optionally substituted by one or more fluoro atoms);

R³, $R^{3a}$ and R⁴ independently represent hydrogen, chloro, bromo, fluoro, $C_{1-3}$-alkyl (which latter alkyl group is optionally substituted by one or more fluoro atoms);

R⁶ represents hydrogen; $C_{1-4}$ alkyl optionally substituted by one or more fluoro atoms;

A represents phenyl, 2-pyridyl, 5- or 6-membered heterocycloalkyl, $C_{3-7}$ cycloalkyl, $C_{5-8}$ linear or branched alkyl (all of which groups are optionally substituted by one or more substituents selected from R⁹); or benzyl, pyridin-2-yl-methylene (which latter two groups are optionally substituted by one or more groups selected from $C_{1-7}$ alkyl (optionally substituted by one or more substituents selected from fluoro and —$OR^{x2}$), halo, —CN and/or —O—$C_{1-7}$ alkyl (optionally substituted by one or more fluoro atoms));

R⁹ represents halo, —O—$C_{1-4}$ alkyl, $C_{1-4}$ alkyl, $C_{3-5}$ cycloalkyl, (which latter three groups are optionally substituted by one or more fluoro atoms;

or a pharmaceutically acceptable salt thereof.

17. A compound according to claim 1, selected from the following compounds, or a pharmaceutically acceptable salt thereof:

| Compound Number | Compound Name |
|---|---|
| 83 | 2-(2,6-Dichloro-phenylamino)-3H-imidazo[4,5-c]pyridine-6-carboxylic acid (4,4-dimethyl-cyclohexyl)-amide; |
| 137 | 2-(2,6-Dichloro-phenylamino)-3H-imidazo[4,5-c]pyridine-6-carboxylic acid-cyclohexyl-amide; |
| 360 | 2-(2-Chloro-6-fluoro-phenylamino)-3-methyl-N-(4-trifluoromethyl-pyridin-2-yl)-3-H-imidazo[4,5-c]pyridine-6-carboxamide; |
| 361 | N-(4-Bromophenyl)-2-(2-chloro-6-fluoro-phenylamino)-3-methyl-3H-iidazo[4,5-c]pyridine-6-carboxamide; |
| 364 | 2-(2,6-Dichlorophenylamino)-3-methyl-N-(4-trifluoromethyl-pyridin-2-yl)-3H-imidazo[4,5-c]pyridine-6-carboxamide; |
| 365 | N-(4-Bromophenyl)-2-(2,6-dichlorophenylamino)-3-methy1-3H-imidazo[4,5-c]pyridine-6-carboxamide; |
| 366 | 2-(3,5-Dichloropyridin-4-ylamino)-N-(4-trifluoromethyl-pyridin-2-yl)-1H-imidazo[4,5-c]pyridine-6-carboxamide; |
| 389 | 2-(2-Chloro-6-fluorophenylamino)-N-(4,4-dimethylcyclohexyl)-3-methyl-3H-imidazo[4,5-c]pyridine-6-carboxamide; |
| 396 | N-(4-tert.-Butyl-pyridin-2-yl)-2-(2,6-dichlorophenylamino)-1H-imidazo[4,5-c]pyridine-6-carboxamide; |
| 406 | 2-(2,6-Dichlorophenylamino)-N-(4,4-dimethylcyclohexyl)-3-methyl-3H-imidazo[4,5-c]pyridine-6-carboxamide; |
| 414 | 2-(2,6-Dichlorophenylamino)-N-(4-trifluoromethyl-pyridin-2-yl)-1H-imidazo[4,5-c]pyridine-6-carboxamide; |
| 417 | 2-(2-Chloro-6-fluoro-phenylamino)-3-methyl-N-(spiro[2.5]octan-6-yl)-3H-imidazo[4,5-c]pyridine-6-carboxamide; |
| 424 | 2-(2,6-Dichlorophenylamino)-3-methyl-N-((1r,4r)-4-trifluoromethyl-cyclohexyl)-3H-imidazo[4,5-c]pyridine-6-carboxamide; |
| 425 | 2-(2,6-Dichlorophenylamino)-3-methyl-N-(spiro[2.5]octan-6-yl)-3H-imidazo[4,5-c]pyridine-6-carboxamide; |
| 427 | N-(4-Chloro-5-methyl-pyridin-2-yl)-2-(2,6-dichlorophenylamino)-1H-imidazo[4,5-c]pyridine-6-carboxamide; |
| 431 | 2-(2-Chloro-6-fluorophenylamino)-3-methyl-N-((1r,4r)-4-trifluoromethyl-cyclohexyl)-3H-imidazo[4,5-c]pyridine-6-carboxamide; |
| 440 | N-(4-(Cyclopentyloxy)pyridin-2-yl)-2-(2,6-dichlorophenylamino)-1H-imidazo[4,5-c]pyridine-6-carboxamide; |
| 444 | 2-(2-Chloro-6-fluorophenylamino)-N-cyclohexyl-3-methyl-3H-imidazo[4,5-c]pyridine-6-carboxamide; |
| 445 | N-(4-Cyclopropylpyridin-2-yl)-2-(2,6-dichlorophenylamino)-1H-imidazo[4,5-c]pyridine-6-carboxamide; |
| 451 | 2-(2,6-Dichlorophenylamino)-N-(spiro[2.5]octan-6-yl)-1H-imidazo[4,5-c]pyridine-6-carboxamide; |
| 462 | N-(4-Cyclopropylpyridin-2-yl)-2-(2,6-dichlorophenylamino)-3-methyl-3H-imidazo[4,5-c]pyridine-6-carboxamide |
| 463 | N-(4-Bromophenyl)-2-(2,6-dichlorophenylamino)-3-methyl-3H-imidazo[4,5-b]pyridine-6-carboxamide; |
| 472 | N-(4-Bromophenyl)-2-(3,5-dichloropyridin-4-ylamino)-3-methyl-3H-imidazo[4,5-c]pyridine-6-carboxamide; |
| 477 | 2-(2,6-Dichlorophenylamino)-N-(2-trifluoromethyl-benzyl)-1H-imidazo[4,5-c]pyridine-6-carboxamide; |
| 478 | 2-(3,5- Dichloropyridin-4-ylamino)-N-(4,4-dimethylcyclohexyl)-3-methyl-3H-imidazo[4,5-c]pyridine-6-carboxamide; |
| 481 | 2-(2,6-Dichlorophenylamino)-N-((1r,4r)-4-trifluoromethyl-cyclohexyl)-1H-imidazo[4,5-c]pyridine-6-carboxamide; |
| 482 | 2-(3,5- Dichloropyridin-4-ylamino)-3-methyl-N-(4-trifluoromethyl-pyridin-2-yl)-3H-imidazo[4,5-c]pyridine-6-carboxamide; |
| 487 | N-Cyclohexyl-2-(2,6-dichlorophenylamino)-3-methyl-3H-imidazo[4,5-c]pyridine-6-carboxamide; |
| 495 | 2-(2,6-Dichlorophenylamino)-N-(4-(tetrahydrofuran-3-yl-oxy)-pyridin-2-yl)-1H-imidazo[4,5-c]pyridine-6-carboxamide; |
| 504 | 2-(2-Chloro-6-fluorophenylamino)-3-methyl-N-((3-trifluoromethyl-pyridin-2-yl)-methyl)-3H-imidazo[4,5-c]pyridine-6-carboxamide; |
| 509 | 2-(2,6- Dichlorophenylamino)-N-((3-trifluoromethyl-pyridin-2-yl)methyl)-1H-imidazo[4,5-c]pyridine-6-carboxamide; |
| 515 | 2-(3,5-Dichloropyridin-4-ylamino)-3-methyl-N-((1r,4r)-4-trifluoromethyl-cyclohexyl)-3H-imidazo[4,5-c]pyridine-6-carboxamide; |
| 522 | 2-(2-Chloro-6-fluorophenylamino)-N-((3-cyclopropylpyridin-2-yl)-methyl)-3-methyl-3H-imidazo[4,5-c]pyridine-6-carboxamide; |

| Compound Number | Compound Name |
|---|---|
| 528 | 2-(2,6- Dichlorophenylamino)-3-methyl-N-((3-trifluoromethyl-pyridin-2-yl)-methyl)-3H-imidazo[4,5-c]pyridine-6-carboxamide; |
| 550 | 2-(3,5- Dichloropyridin-4-ylamino)-3-methyl-N-((3-trifluoromethyl-pyridin-2-yl)-methyl)-3H-imidazo[4,5-c]pyridine-6-carboxamide; |
| 716 | 2-(2,6-Dichlorophenylamino)-N-(4,6-dimethyl-pyridin-2-yl)-1H-imidazo[4,5-c]pyridine-6-carboxamide; |
| 717 | 2-(2,6-Dichlorophenylamino)-N-(4,5-dimethyl-pyridin-2-yl)-1H-imidazo[4,5-c]pyridine-6-carboxamide; |
| 718 | 2-(2,6-Dichlorophenylamino)-N-(5-chloro-4-methyl-pyridin-2-yl)-1H-imidazo[4,5-c]pyridine-6-carboxamide; |
| 719 | 2-(2,6-Dichlorophenylamino)-N-(5-fluoro-4-methyl-pyridin-2-yl)-1H-imidazo[4,5-c]pyridine-6-carboxamide; |
| 720 | 2-(2,6-Dichlorophenylamino)-N-(5-trifluoromethyl-pyridin-2-yl)-1H-imidazo[4,5-c]pyridine-6-carboxamide; |
| 721 | 2-(2,6-Dichlorophenylamino)-N-(2,2,3,3,4,4,5,5,6,6,7,7,8,8,8-pentadecafluoro-octyl)-1H-imidazo[4,5-c]pyridine-6-carboxamide; |
| 722 | 2-(2,6-Dichlorophenylamino)-N-(4-bromo-phenyl)-1H-imidazo[4,5-c]pyridine-6-carboxamide; |
| 723 | 2-(2,6-Dichlorophenylamino)-N-(6-methyl-4-trifluoromethyl-pyridin-2-yl)-1H-imidazo[4,5-c]pyridine-6-carboxamide; |
| 724 | 2-(2,6-Dichlorophenylamino)-3-methyl-N-(4,5-dimethyl-pyridin-2-yl)-3H-imidazo[4,5-c]pyridine-6-carboxamide; |
| 725 | 2-(2,6-Dichlorophenylamino)-N-(5-cyclopropyl-pyridin-2-yl)-1H-imidazo[4,5-c]pyridine-6-carboxamide; |
| 726 | 2-(2,6-Dichlorophenylamino)-3-methyl-N-(5-chloro-4-methyl-pyridin-2-yl)-3H-imidazo[4,5-c]pyridine-6-carboxamide; |
| 727 | 2-(2-Fluoro-6-trifluoromethyl-phenylamino)-N-(4-trifluoromethyl-pyridin-2-yl)-1H-imidazo[4,5-c]pyridine-6-carboxamide; |
| 728 | 2-(2-Chloro-6-trifluoromethyl-phenylamino)-N-(4-trifluoromethyl-pyridin-2-yl)-1H-imidazo[4,5-c]pyridine-6-carboxamide; |
| 729 | 2-(2-Chloro-6-fluoro-phenylamino)-N-(4-trifluoromethyl-pyridin-2-yl)-1H-imidazo[4,5-c]pyridine-6-carboxamide; |
| 730 | 2-(2,6-Dichloro-4-fluoro-phenylamino)-N-(4-trifluoromethyl-pyridin-2-yl)-1H-imidazo[4,5-c]pyridine-6-carboxamide; |
| 731 | 2-(2-Chloro-4,6-difluoro-phenylamino)-N-(4-trifluoromethyl-pyridin-2-yl)-1H-imidazo[4,5-c]pyridine-6-carboxamide; |
| 732 | 2-(3,5-Dichloro-pyridin-4-yl-amino)-N-(4-bromo-phenyl)-1H-imidazo[4,5-c]pyridine-6-carboxamide; |
| 733 | 2-(3,5-Dichloro-pyridin-4-yl-amino)-N-(6-methyl-4-trifluoromethyl-pyridin-2-yl)-1H-imidazo[4,5-c]pyridine-6-carboxamide; |
| 734 | 2-(4-Trifluoromethyl-pyridin-3-ylamino)-3-methyl-N-(4-trifluoromethyl-pyridin-2-yl)-3H-imidazo[4,5-c]pyridine-6-carboxamide; |
| 735 | 2-(3,5-Dichloro-pyridin-4-yl-amino)-N-(4-cyclopropyl-5-methyl-pyridin-2-yl)-1H-imidazo[4,5-c]pyridine-6-carboxamide; |
| 736 | 2-(3,5-Dichloro-pyridin-4-yl-amino)-N-(6-chloro-4-trifluoromethyl-pyridin-2-yl)-1H-imidazo[4,5-c]pyridine-6-carboxamide; |
| 737 | 2-(3,5-Dichloro-pyridin-4-yl-amino)-N-(5-isopropyl-pyridin-2-yl)-1H-imidazo[4,5-c]pyridine-6-carboxamide; |
| 738 | 2-(3,5-Dichloro-pyridin-4-yl-amino)-N-(4-cyclobutyl-pyridin-2-yl)-1H-imidazo[4,5-c]pyridine-6-carboxamide; |
| 739 | 2-(3,5-Dichloro-pyridin-4-yl-amino)-N-(6-dimethylamino-4-trifluoromethyl-pyridin-2-yl)-1H-imidazo[4,5-c]pyridine-6-carboxamide; |
| 740 | 2-(3,5-Dichloro-pyridin-4-yl-amino)-N-(6-cyclopropyl-4-trifluoromethyl-pyridin-2-yl)-1H-imidazo[4,5-c]pyridine-6-carboxamide. |

18. A pharmaceutical formulation comprising a compound according to claim 1, or a pharmaceutically-acceptable salt thereof, and a pharmaceutically acceptable adjuvant, diluent or carrier.

\* \* \* \* \*